(12) United States Patent
Miyazaki

(10) Patent No.: US 6,782,286 B2
(45) Date of Patent: *Aug. 24, 2004

(54) MRI SYSTEM AND MR IMAGING METHOD

(75) Inventor: Mitsue Miyazaki, Otawara (JP)

(73) Assignee: Kabushiki Kaisha Toshiba, Kawasaki (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/294,148

(22) Filed: Apr. 20, 1999

(65) Prior Publication Data

US 2003/0171671 A1 Sep. 11, 2003

(30) Foreign Application Priority Data

Apr. 20, 1998 (JP) .......................................... 10-108909

(51) Int. Cl.⁷ .............................................. A61B 5/055
(52) U.S. Cl. ....................... 600/410; 600/413; 600/419; 324/306; 324/307; 324/309
(58) Field of Search ................................ 600/413, 419, 600/410; 324/307, 306, 309

(56) References Cited

U.S. PATENT DOCUMENTS

| | | |
|---|---|---|
| 5,050,609 A | 9/1991 | Balaban et al. |
| 5,777,473 A | 7/1998 | Takai et al. |
| 5,891,032 A * | 4/1999 | Harvey ........................ 600/419 |
| 6,009,341 A * | 12/1999 | Edelman ...................... 600/413 |
| 6,043,655 A * | 3/2000 | Makita et al. ............... 324/309 |
| 6,144,201 A * | 11/2000 | Miyazaki .................... 324/306 |

FOREIGN PATENT DOCUMENTS

EP 0 599 456 A1 * 6/1994

OTHER PUBLICATIONS

Forsen et al, "Study of Moderately Rapid Chemical Exchange Reactions by Means of Nuclear Magnetic Double Resonance", The Journal of Chemical Physics, vol. 19, No. 11, Dec. 1, 1963.

(List continued on next page.)

*Primary Examiner*—Ruth S. Smith
(74) *Attorney, Agent, or Firm*—Nixon & Vanderhye P.C.

(57) ABSTRACT

Without injecting a contrast medium, blood pumped out from the heart can preferably be depicted in a non-invasive fashion, resulting in a greatly shortened scanning time for data acquisition. An MRI system temporal phase detector acquires an ECG signal of an object, and an imaging scanner performs a three-dimensional scanning pulse sequence every slice encoding in synchronism with an ECG signal. The pulse sequence includes an RF excitation pulse for which a repetition time is set to be shorter than conventional. In addition, the pulse sequence includes a slice-directional gradient for performing data acquisition based on the slice encoding in an approximately parallel direction to a running direction of blood flow. Furthermore, the pulse sequence includes a phase-encoding directional gradient for applying phase encoding in a direction approximately coinciding with a running direction of the blood flow.

20 Claims, 20 Drawing Sheets

OTHER PUBLICATIONS

Pike et al, "Magnetization Transfer Time–of–Flight Magnetic Resonance Angiography", Magnetic Resonance in Medicine 25, 371–379 (1992).

Miyazaki et al, "A Novel Saturation Transfer Contrast Method for 3D Time–of–Flight Magnetic Resonance Angiography: A Slice–Selective Off–Resonance Sinc Pulse", Magnetic Resonance in Medicine 32, 52–59, 1994.

Wolff et al, "Magnetization Transfer Imaging: Practical Aspects and Clinical Applications", Radiology 1994, 192:593–599.

Hatabu et al, Pulmonary Perfusion:Qualitative Assessment with Dynamic Contrast–Enhanced RI Using Ultra–Short TE and Inversion Recovery Turbo FLASH, MRM 36:503–508 (1966).

Edelman et al, "Noninvasive Assessment of Regional Ventilation in the Human Lung Using Oxygen–Enhanced Magnetic Resonance Imaging", Nature Medicine, vol. 2, 11 (1996).

Miyazaki, "A Novel MR Angiography Technique:SPEED Acquisition Using Half–Fourier RARE", JMRI 1998; 8:505–507.

* cited by examiner (a)  (b)

BEFORE ADMINISTRATION OF ACETIC ACID

Bthin — AFTER ADMINISTRATION OF ACETIC ACID

MRI SYSTEM AND MR IMAGING METHOD

BACKGROUND OF THE INVENTION

1. Field of the Invention

The present invention relates to magnetic resonance imaging for internally imaging a subject to be examined on the basis of magnetic resonance phenomena occurring in the subject. More particularly, this invention is concerned with an MRI (magnetic resonance imaging) system and MR (magnetic resonance) imaging method directed to MR angiography, in which echo signals are acquired during a shorter imaging period using electrocardiogram gating having an appropriate delay time in order to depict flows of blood, with no contrast medium.

Though the presently described embodiments of this invention have been put into practice to image blood flows in an object, the imaging techniques described can also be applied to image cerebral spinal fluid (CSF) or other fluids that move within the object.

2. Description of the Related Art

Magnetic resonance imaging is based on an imaging technique for magnetically exciting nuclear spins in a subject positioned in a static magnetic field by applying a radio-frequency (RF) signal of the Larmor frequency, and reconstructing an image using MR signals induced by the excitation.

In the field of this magnetic resonance imaging, when blood flow images of the pulmonary field or abdomen are obtained clinically, MR angiography has been used, in which a contrast medium is injected into a subject to produce contrast in blood. However, this contrast MR angiography needs an invasive treatment to inject the contrast medium, thus, first of all, mental and physical burdens on patients become large. Such examination cost is also high. Additionally, there are some cases where the contrast medium cannot be injected on account of patient's physical characteristics.

In cases the contrast medium cannot be injected, other imaging techniques are used alternatively. Such techniques include a time-of-flight (TOF) method and a phase contrast (PC) method. Effects of flow in magnetic resonance imaging are attributed to either of two natures possessed by spins in motion. One is that spins simply move their positions and the other results from phase shift of transverse magnetization caused when spins move in a gradient field. Of these, the former attributed to the position movement is the basis of the TOF technique and the latter attributed to the phase shift is that of phase contrast technique.

However, even when the above TOF technique or phase contrast technique is used, in obtaining MR images in the pulmonary field or the abdomen, the depiction of flows in the superior-inferior direction of such large vessels as the aorta requires imaging to be conducted vertically to its flow direction. That is, axial images are acquired along the slice direction set to the superior-inferior direction. In the three-dimensional imaging based on this, the number of imaging slices becomes large, resulting in that the entire imaging time is substantially longer.

SUMMARY OF THE INVENTION

The present invention attempts to break through the foregoing current situations, and its one object is to, without injection of a contrast medium, obtain MRA images in a non-invasive manner and remarkably shorten the imaging time.

Another object of the present invention is to, without injection of a contrast medium, namely, non-invasively, steadily depict flow of blood pumped out by the heart and remarkably shorten an imaging time to acquire data necessary for this depiction.

Still another object of the present invention is to, without injection of a contrast medium, namely, non-invasively, steadily depict images in which arteries and veins are separated and remarkably shorten an imaging time to acquire data necessary for this depiction.

Still another object of the present invention is to, without injection of a contrast medium, namely, non-invasively, steadily raise a depiction performance of the running direction of vessels and greatly shorten an imaging time to acquire data necessary for this depiction.

MR angiography technique according to the present invention is referred to as an "FBI (Fresh Blood Imaging) technique," because fresh blood that has just pumped out from the heart can always be scanned. Specifically, this FBI technique is conducted in a manner such that ECG-gating whose delay time is appropriately set is applied in order to restlessly trace fresh and stable, but high speed, blood that has just pumped from the heart every R-wave, the repetition time TR for each slice encode is set to a shorter time so as to bring the longitudinal relaxation of magnetization in stationary parenchyma into an insufficient state on purpose, and, if necessary, IR (inversion recovery) pulses and/or fat suppression pulses are used to suppress signals emanating from fat, all these being included in three-dimensional scanning to suppress signals from parenchyma, depicting flow of blood. This permits vessels (flows of blood) to be depicted steadily with no contrast medium injected.

The three-dimensional scanning used in the present invention is scanning for imaging a volume region of a subject. This scanning is not confined to scanning referred to as the three-dimensional Fourier transform method, but includes scanning based on a multi-slice method by which a plurality of slices are imaged on the two-dimensional Fourier transform method. In the event that the present invention is practiced under the multi-slice method, synchronous timing to a signal indicative of the cardiac temporal phase is set to the same for each slice.

Particularly, it is desirable to set the slice direction so that, for each slice encoding, data can be acquired along a nearly parallel direction to the running direction of blood vessels. It is also desirable to make the phase-encoding direction agree with the running direction of blood vessels. These shorten the imaging time, unlike the TOF or phase contrast technique. Calculating differences of imaged data, for example, twice with changed delay times of the ECG gating is able to provide MRA images of which arteries and veins are separated.

"A shorter repetition time TR" stated in the present invention, which should be compared with a repetition time (approx. 5000 to 8000 ms) used by a FASE (Fast Asymmetric SE) method based on the conventional methods, such as MRCP (MR CholangioPancreatography), used for imaging regions of which T2 time is longer, means that it is shorter than such repetition time. "The shorter repetition time TR" is directed to put the longitudinal magnetization of spins of stationary parenchyma into an unsatisfactory state on purpose. From a comparison with the conventional methods, "the shorter repetition time TR" in the present invention is set to a value not more than four heartbeats (4R-R).

From a detailed construction viewpoint, the fundamental construction of an MRI system according to the present invention is a system that provides a blood flow image from a region to be imaged of the object and is characteristic of comprising temporal phase detecting means for detecting a signal indicative of cardiac temporal phases of an object and imaging scanning means for performing a three-dimensional scanning pulse sequence every slice encoding in synchronism with the signal indicative of the cardiac temporal phases.

Preferably, the pulse sequence includes an RF excitation pulse of which repetition time is set to be shorter. Additionally, the pulse sequence includes a slice-directional gradient for performing data acquisition based on the slice encoding in an approximately parallel direction to a running direction of the blood flow. Furthermore, the pulse sequence includes a phase-encoding directional gradient for applying a phase encode in a direction approximately coinciding with a running direction of the blood flow.

For example, the three-dimensional scanning pulse sequence is a pulse sequence according to a three-dimensional Fourier transform method or a multi-slice method for imaging a volume region.

Further, bay way of example, the temporal phase detecting means are means for acquiring an ECG signal of the object as the signal indicative of the cardiac temporal phases and the imaging scanning means are means that perform the pulse sequence in synchronism with an R-wave appearing in the ECG signal. For instance, the repetition time is an interval corresponding to four or less times of an appearance period of the R-wave.

Additionally, there may be provided an MRI system comprising preparing scanning means for acquiring a plurality of sets of echo signals by performing a preparing scan with a region to be imaged of the object at each of mutually different delay times set from the R-wave of the ECG signal and preparing-image producing means for producing the plurality of images form the echo signals, wherein the imaging scanning means have means for obtaining an optimum value of the delay times, determined on the basis of the plurality of images, and means for performing the pulse sequence with the object in synchronism with the optimum delay time.

On one hand, an MRI system may comprises preparing scanning means for acquiring a plurality of sets of echo signals by performing a preparing scan with a region to be imaged of the object at each of mutually different cardiac temporal phases determined based on the signal indicative of the cardiac temporal phases and preparing-image producing means for producing the plurality of images form the echo signals, wherein the imaging scanning means have means for obtaining an optimum cardiac temporal phase among the plurality of cardiac temporal phases, determined on the basis of the plurality of images, and means for performing the pulse sequence with the object in synchronism with the temporal phase.

Also, the imaging scanning means may comprise scan performing means for not only performing the pulse sequence a plurality of times with a synchronous timing to the signal changed but also obtaining a plurality of sets of image data, and data processing means for obtaining, from the plurality-of-sets image data, image data of which artery and vein as the blood flow are separated to each other. In this case, the data processing means that comprises difference calculating means for weighting the plurality-of-sets image data and performing mutual difference calculation with the image data, obtaining one set of difference image data, and producing means for producing from the one set of difference image data a final image depicting the blood flow. For example, the producing means are a process performing a maximum intensity projection (MIP) from the one set of difference image data.

Furthermore, in each of the above constructions, it is preferred that there are provided breath holding instructing means that instructing the object to hold one's breath at least during a period through which the imaging scanning means perform the pulse sequence.

In the fundamental construction of the present invention, it may also be possible that there are provided breath cycle detecting means for detecting a breath cycle of the object, wherein the imaging scanning means are means that perform the pulse sequence in synchronism with the signal detected by the temporal phase detecting means and the breath cycle detected by the breath cycle detecting means.

In the fundamental construction of the present invention, it may also be possible that the temporal phase detecting means and the imaging scanning means are brought into operation with a reagent administered into the object. For example, the reagent is a reagent to provide a blood flow in the object with contrast effects. This reagent is, for example, physiological saline or glucose. Meanwhile, the reagent may be a reagent to stimulate a blood vessel of the object. This reagent is acetic acid or potable material including acetic acid.

In the above fundamental construction, there may be provided means for performing the imaging scan before and after administering a reagent into the object, respectively, so that a plurality of sets of MR signals are obtained and means for producing a blood flow image of the object from the plurality of sets of MR signals.

Additionally, in each construction above, preferably, the pulse sequence consists of a pulse train formed based on an FSE method, FASE method, or EPI method.

On one hand, an MR imaging method according to the present invention is a method of depicting a blood flow in a region to be imaged of an object, wherein a signal indicative of cardiac temporal phases of the object is acquired, and a three-dimensional scanning pulse sequence is performed with the region of the object every slice encoding in synchronism with a reference wave of the signal.

By way of example, the pulse sequence includes an RF pulse of which repetition time is set to be shorter. Further, the pulse sequence includes a slice-directional gradient for performing data acquisition based on the slice encoding in an approximately parallel direction to a running direction of the blood flow. Further, the pulse sequence includes a phase-encoding directional gradient for applying a phase encode in a direction approximately coinciding with a running direction of the blood flow.

DETAILED DESCRIPTION OF THE PREFERRED EMBODIMENTS

Hereinafter, embodiments of the present invention will be explained.

(First Embodiment)

A first embodiment of the present invention will now be described with reference to FIGS. 1 to 10.

Figure 1:
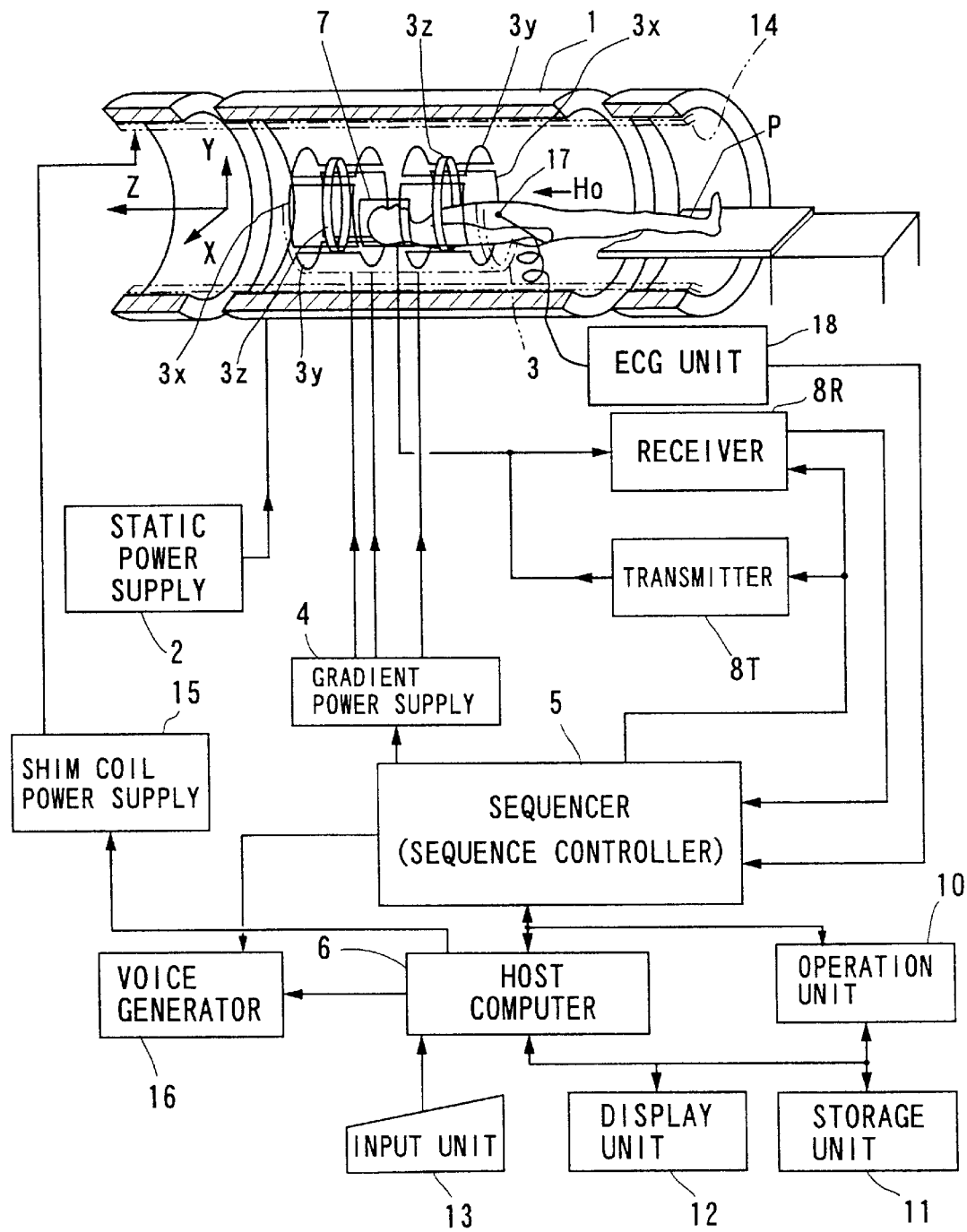
FIG. 1 is a functional block diagram showing one example of the configuration of an MRI system according to an embodiment of the present invention.

FIG. 1 shows the outlined configuration of an MRI (magnetic resonance imaging) system in accordance with the embodiment.

The MRI system comprises a patient couch on which a patient P lies down, static magnetic field generating components for generating a static magnetic field, magnetic field gradient generating components for appending positional information to a static magnetic field, transmitting/receiving components for transmitting and receiving a radio-frequency signal, control and operation components responsible for both control of the whole system and image reconstruction, and electrocardiogram components for acquiring an ECG signal of a patient, the ECG signal being employed as a signal indicative of cardiac temporal phases of the patient.

The static magnetic field generating components includes a magnet 1 that is of, for example, a superconducting type and a static power supply 2 for supplying a current to the magnet 1, and generates a static magnetic field $H_0$ in an axial direction (Z-axis direction) in a cylindrical bore (diagnostic space) into which the patient P is inserted. The magnet unit includes shim coils 14. A current used to homogenize a static magnetic field is supplied from a shim coil power supply 15 to the shim coils 14 under the control of a host computer to be described later. The couch top of the patient couch on which the patient P lies down can be inserted into the bore of the magnet 1 so that the couch top can be withdrawn.

The magnetic field gradient generating components includes a gradient coil unit 3 incorporated in the magnet 1. The gradient coil unit 3 includes three pairs (kinds) of x-, y- and z-coils $3x$ to $3z$ used to generate magnetic field gradients changing in strength in X-axis, Y-axis, and Z-axis directions that are mutually orthogonal. The magnetic field gradient generating components further includes a gradient power supply 4 for supplying currents to the x-, y-, and z-coils $3x$ to $3z$. The gradient power supply 4 supplies pulsated currents used to generate magnetic field gradients to the x-, y-, and z-coils $3x$ to $3z$ under the control of a sequencer that will be described later.

The pulsated currents supplied from the gradient power supply 4 to the x-, y-, and z-coils $3x$ to $3z$ are controlled, whereby magnetic field gradients changing in the three X-, Y-, and Z-directions (physical axis directions) are synthesized. Thus, a slice-directional magnetic field gradient $G_s$, a phase-encoding-directional magnetic field gradient $G_e$, and a readout-directional (frequency-encoding-directional) magnetic field gradient $G_r$, which are mutually orthogonal, can be specified and changed arbitrarily about each of their logic axis directions. The magnetic field gradients to be applied in the slice direction, the phase-encoding direction, and the readout direction are superposed on the static magnetic field $H_0$.

The transmitting/receiving components includes an RF coil 7 located in the vicinity of a patient P in the diagnostic space inside the magnet 1, and a transmitter 8T and a receiver 8R both connected to the coil 7. The transmitter 8T and the receiver 8R operate under the control of a sequencer 5 described later. The transmitter 8T supplies to the RF coil 7 RF current pulses of the Larmor frequency, which are used to excite the nuclear magnetic resonance (NMR). The receiver 8R takes in MR signals (radio-frequency signals) received by the RF coil 7, carries out various kinds of signal processing, such as pre-amplification, intermediate-frequency conversion, phase detection, low-frequency amplification, and filtering, with the echo signals, and A/D-converts them into digital data (raw data) of the MR signals.

Furthermore, the control and operation components includes a sequencer 5 (also referred to as a sequence controller), a host computer 6, an operation unit 10, a storage unit 11, a display unit 12, an input unit 13, and a voice generator 16. Of them, the host computer 6 provides the sequencer 5 with pulse sequence information and manages the operations of the entire system, according to software procedures memorized.

Figure 2:
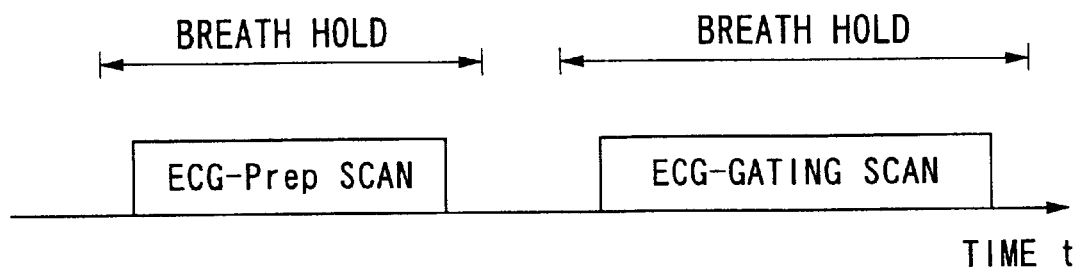
FIG. 2 explains the time-sequential relationship between an ECG-prep scan and an imaging scan based on an electrocardiogram gating technique performed in the embodiment.
Figure 3:
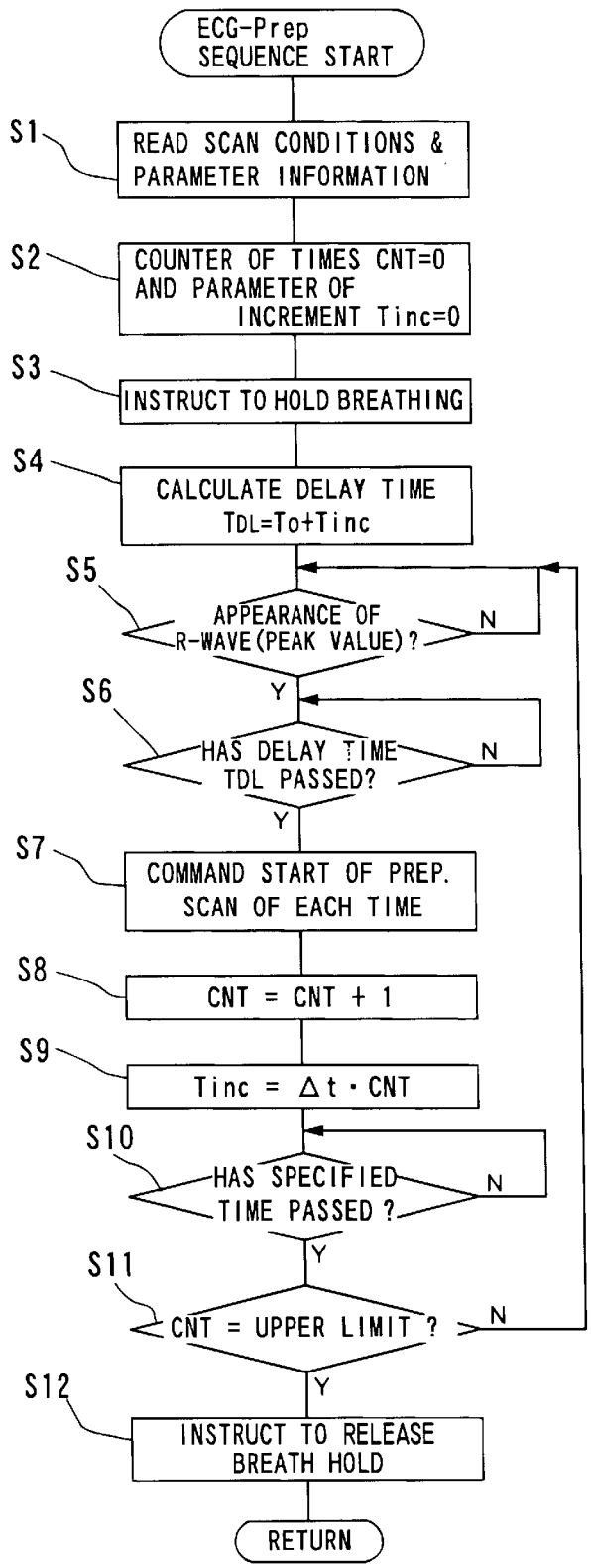
FIG. 3 is an outlined flowchart exemplifying the procedures of the ECG-prep scan performed by a host computer.
Figure 7:
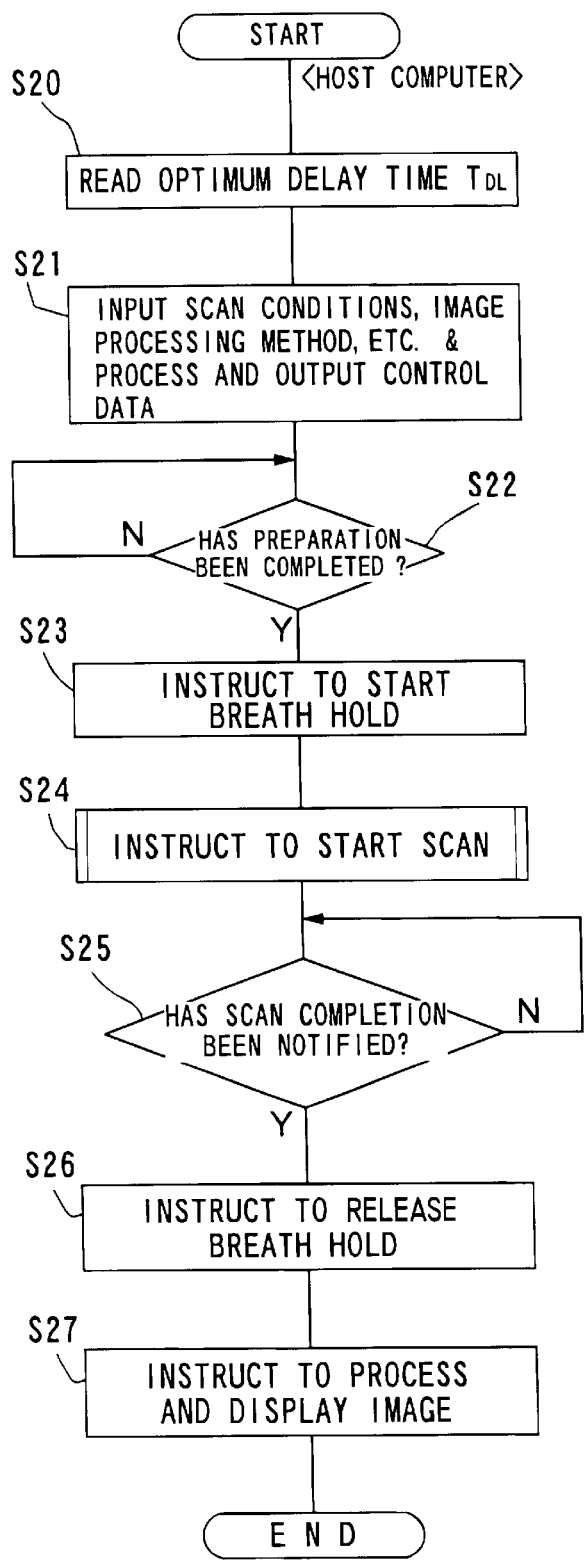
FIG. 7 is an outlined flowchart exemplifying control of the imaging scan executed by the host computer.
Figure 8:
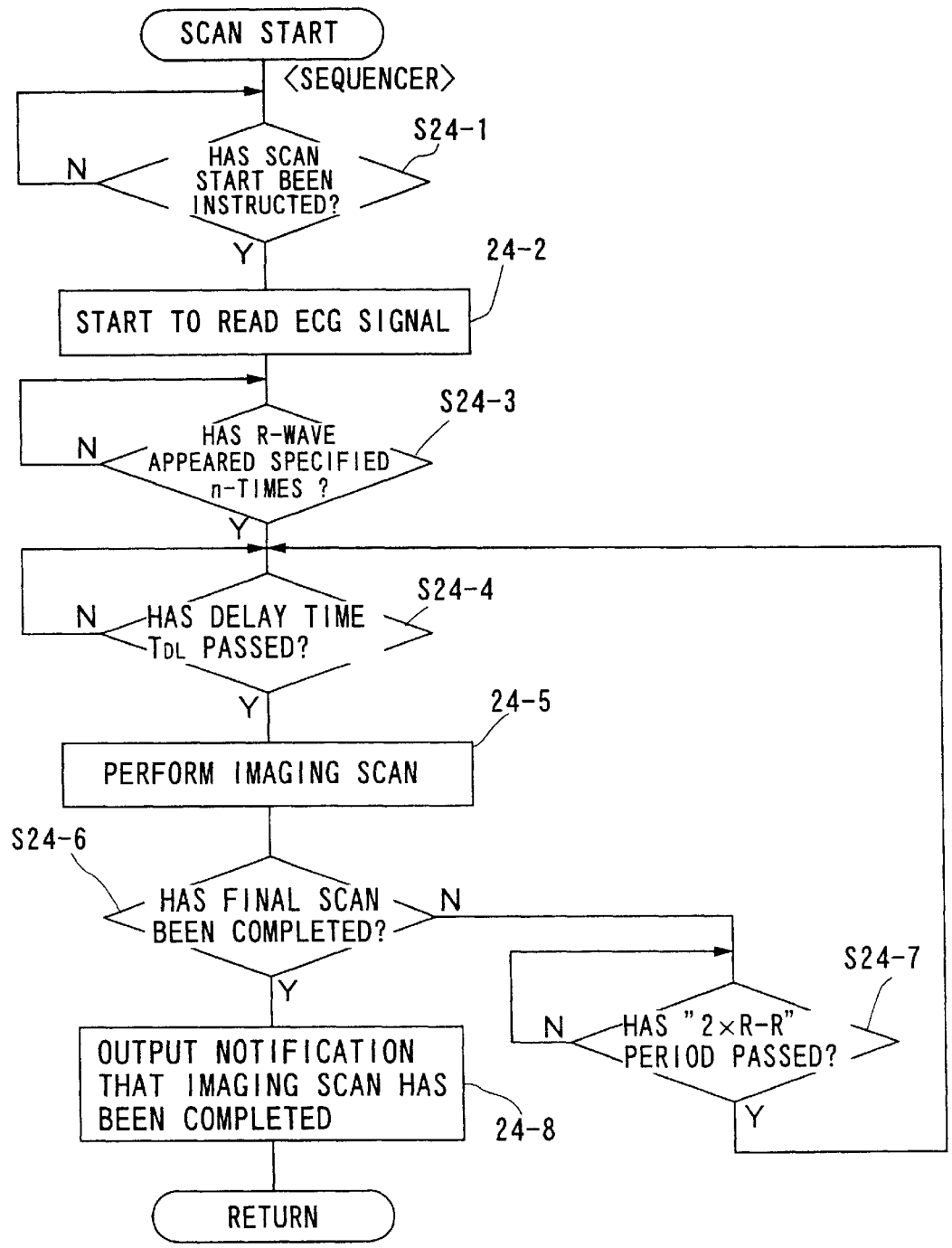
FIG. 8 is an outlined flowchart exemplifying control of the imaging scan executed by a sequencer.

One feature of the MRI system is that a scan based on the electrocardiogram gating technique at previously selected synchronous timing (cardiac temporal phase) is performed. In the main program not shown, the host computer 6 executes, as shown in FIG. 2, a preparing scan (hereinafter referred to as an ECG-prep scan) performing a preparing pulse sequence to decide the synchronous timing in advance and a scan for imaging (hereinafter referred to as an imaging scan) performing an imaging pulse sequence with the electrocardiogram gating on the decided synchronous timing. One example of executed routines of the ECG-prep scan is shown in FIG. 3 and that of the imaging scan with the electrocardiogram gating is shown in FIGS. 7 and 8, respectively.

The sequencer 5, which has a CPU and memories, stores pulse-sequence information sent from the host computer 6, controls the operations of the gradient power supply 4, transmitter 8T, and receiver 8R according to the stored information, and temporarily receives digital data corresponding to MR signals outputted from the receiver 8R so as to transmit them to the operation unit 10. The pulse-sequence information includes all the information required for operating the gradient power supply 4, transmitter 8T, and receiver 8R according to a series of pulse sequences. For example, such information includes information about the strength, duration, and application timing of pulsed currents applied to the x-, y-, and z-coil $3x$ to $3z$.

As to the pulse sequences, provided that a Fourier transform method is adopted, a two-dimensional (2D) scan or a three-dimensional (3D) scan can be used. As examples of pulse trains available to those scans, preferable are pulse trains on a fast SE method, EPI (Echo Planar Imaging) method, FASE (Fast asymmetric SE) method (that is, an imaging technique in which both a fast SE method and a half-Fourier method are combined), or others.

The operation unit 10 receives digital data (original data) sent from the receiver 8R via the sequencer 5, maps the original data (also known as raw data) in a Fourier space (also known as a k-space or frequency space) formed in its incorporated memory, and performs for each set of data a two-dimensional or three-dimensional Fourier transform with the mapped original data so as to reconstruct an image in the real space. Moreover, the operation unit performs synthesizing processing and difference-calculation processing with data of images. The synthesizing processing includes addition of image data of a plurality of frames every corresponding pixel, maximum intensity projection (MIP) processing selecting a maximum among image data of a plurality of frames every corresponding pixel. As another example of the above synthesizing processing, available is a method by which original data of a plurality of frames are synthesized into a frame of original data, as they are, with the axes of the frames matched in the Fourier space. Additionally, the addition includes simple addition, averaging, or weighted addition.

The storage unit 11 can preserve image data produced by the above synthesis processing or difference processing as well as reconstructed image data. The display unit 12 displays an image. By using the input unit 13, an operator is able to provide with the host computer 6 parameter information for selecting desired synchronous timing, scan conditions, the type of a pulse sequence, and information about processing image synthesis and difference.

The voice generator 16 utters, for example, voice messages informing a patient of the start and end of breath hold in response to instructions sent from the host computer 6.

Furthermore, the electrocardiogram components comprises an ECG sensor 17 attached to the patient body to detect an electric ECG signal and an ECG unit 18 performing various processes including digitization with the detected ECG signal and sending it to both the host computer 6 and the sequencer 5. The sequencer 5 to perform each of an ECG-prep scan and an ECG-gating imaging scan uses this measured ECG signal. This enables appropriate setting of synchronous timing on the ECG-gating method, and data acquisition can be done by the ECG-gating imaging scan on the set synchronous timing.

Referring to FIGS. 3 to 6, processing for determining a synchronous timing necessary for the imaging scan on the ECG gating will now be explained.

The host computer 6, which is in operation for a given main program not shown, responds to a command from the input device 13 and commences to execute an ECG-prep scan shown in FIG. 3.

First, the host computer 6 reads from the input device 13 scan conditions and information about parameters both required to perform an ECG-prep scan (step S1 in the figure). The scan conditions include the type of a scan, the type of a pulse sequence, and a phase-encoding direction. Parameter information includes an initial time $T_0$ (herein, defined as a time from an R-wave peak in the ECG signal) to determine an ECG-gating synchronous timing (temporal phase), a time increment $\Delta t$, and an upper limit of a numbering counter CNT. An operator can properly set these parameters.

The host computer 6 then initializes the numbering counter CNT counting the execution times of the sequence and a time increment parameter $T_{inc}$ determining the synchronous timing (CNT=0, $T_{inc}$=0; step S2). After this, the host computer 6 sends message data to the voice generator 16 to generate breath-hold instructions, such as "Hold your breath, please." toward an object (patient) (step S3). It is preferred that the breath hold is performed for suppression of body motions of a patient which may be caused during the ECG-prep scan. However, the ECG-prep scan may be performed with no breath hold in some occasions.

After having completed the above preparation, the host computer 6 sequentially executes processes shown after step S3. This execution permits the scan with the synchronous timing changed in the ECG gating.

Specifically, $T_{DL}=T_0+T_{inc}$ is calculated to obtain a delay time $T_{DL}$ from the peak time instant of an R-wave (step S4). The ECG signal subjected to the signal processing in the ECG unit 18 is then read and it is determined whether or not the R-wave peak value has appeared in the signal (step S5). This determination will be repeated until the R-wave appears. When the R-wave appears (Yes at step S5), it is then determined whether or not the delay time $T_{DL}$ calculated at step S4 has elapsed since the appearance of the R-wave peak time (step S6). This determination will also be repeated until the delay time $T_{DL}$ elapses.

Figure 4:
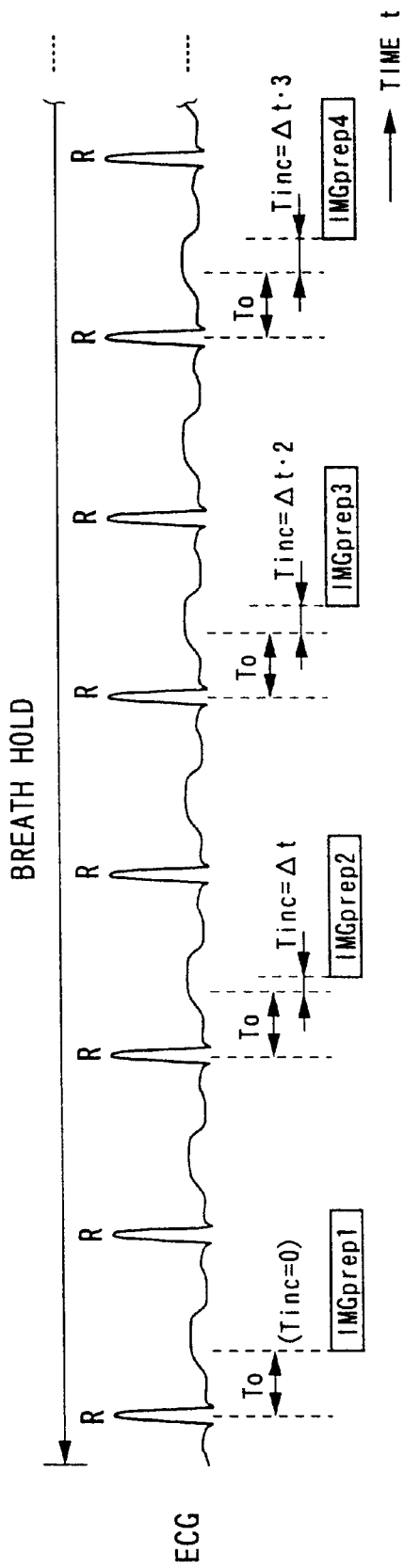
FIG. 4 is a timing chart showing one example of the ECG-prep scan.
Figure 5:
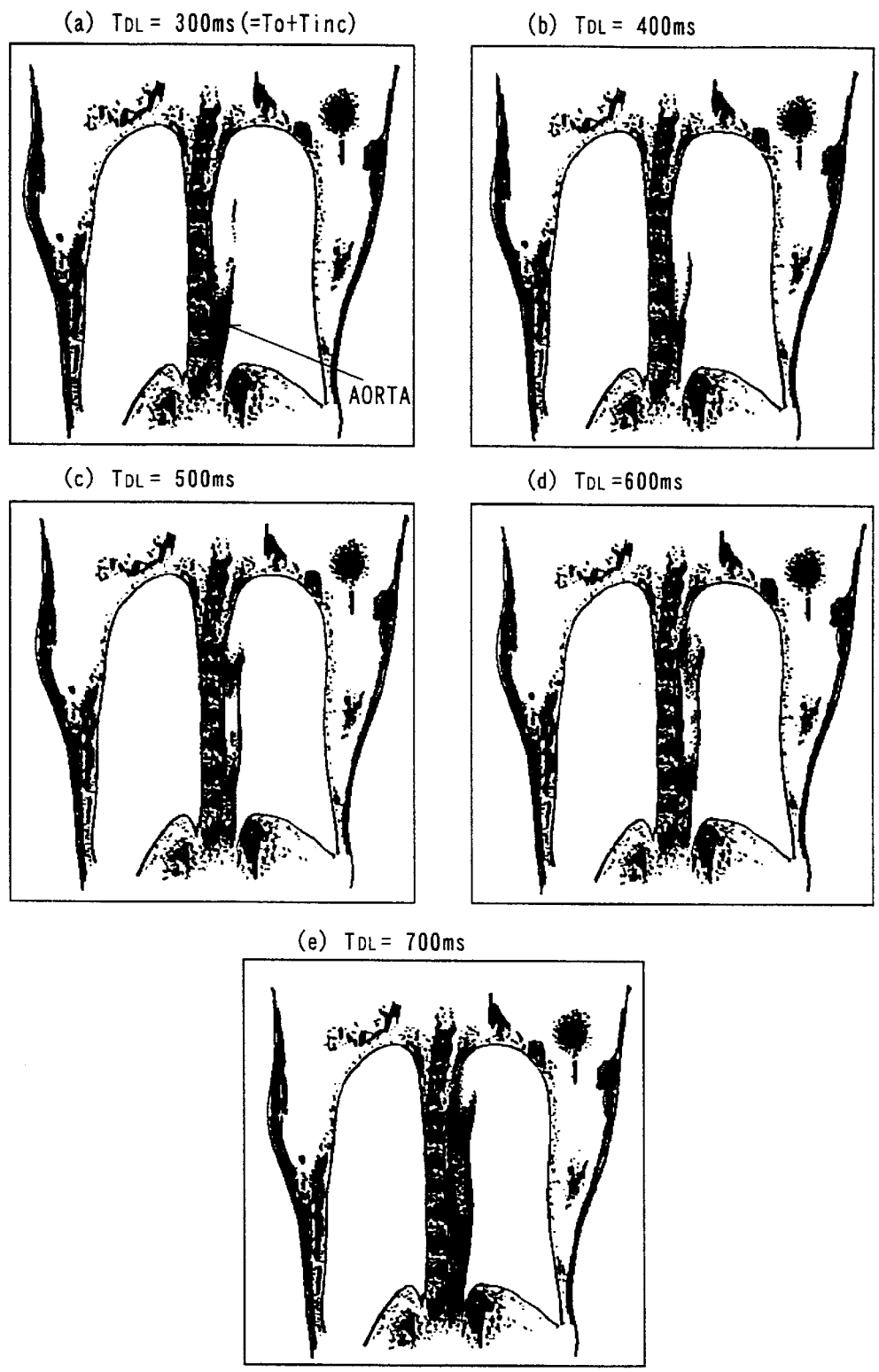
FIG. 5 shows pictorially sketched MRA images of the pulmonary field obtained by the ECG-prep scan whose delay time is dynamically changed.

When the time has passed by the delay time $T_{DL}$ since the R-wave peak time instant (Yes at step S6), the sequencer 5 is ordered to start a pulse sequence of each time (step S7, refer to FIG. 4). It is preferred that this pulse sequence is identical in type to the imaging pulse sequence later described. For example, an available pulse sequence is based on the FASE (Fast Asymmetric SE) technique combining the fast SE method and the half-Fourier method. Of course, a variety of pulse sequences, such as a fast SE method and an EPI method, are usable for this pulse sequence. In response to the instructions, the sequencer 5 commences performing the pulse sequence of which type has been specified by the operator, resulting in that the region of a desired portion in the object is scanned. In the event that, for example, the main scan (imaging scan) for image data acquisition is performed on the three-dimensional (3D) technique, the ECG-prep scan may be either a two-dimensional scan or a three-dimensional scan whose scan region is made to agree with that for the main scan.

After the above sequence has been instructed to start, the numbering counter CNT is incremented such that CNT=CNT+1 (step S8), then the time increment parameter $T_{inc}$ is computed such that $T_{inc}=\Delta t \times CNT$ (step S9). In other words, every time when the pulse sequence is ordered to be executed, the count of the counter CNT increases by one and the increment parameter $T_{inc}$ adjusting the synchronous timing increases in proportion to the count.

Then, a standby state continues until a predetermined period (for example, approx. 500 to 1000 msec) necessary for the execution of the pulse sequence of each time passes (step S10). Then, whether the count of the numbering counter CNT reaches the preset upper limit or not is determined (step S11). In cases where, for example, five two-dimensional images are produced with the delay time $T_{DL}$ changed into various values for the purpose of optimizing the synchronous timing, the count in the counter CNT is set to "5". If the count has not yet reached the upper limit (No at step S11), the processing is returned to step S5 to repeat the above processing. In contrast, the count in the counter CNT equals the upper limit (Yes at step S11), a command to release the breath hold is sent to the voice generator 16 (step S12), and the processing returns to the main program. A voice message to release the patient from the breath hold is such that "you can breathe."

Executing the above processes sequentially leads to the execution of a preparing pulse sequence of which timing is exemplified in FIG. 4. For example, when the initial time $T_0=300$ msec and the time interval $\Delta T=100$ msec are set, the delay time $T_{DL}$ to determine the synchronous timing is adjusted to 300 msec for the first time of scanning, 400 msec for the second time of scanning, 500 msec for the third time of scanning, and so on. Therefore, when the first R-wave peak appears after the instructions of the breath hold, the first scan $IMG_{prep1}$ based on, for example, the FASE method is executed so that it lasts for a certain period (for example, approx. 500 to 1000 msec) from a certain time instant when the delay time $T_{DL}(=T_0)$ has elapsed after the R-wave peak appearance, whereby echo signals being acquired. Whenever the next R-wave may appear during the continuation of this sequence, the foregoing waiting process at step S10 in FIG. 3 makes the sequence continue regardless of the R-wave that appeared in the course of execution. Namely, once the sequence starts in synchronization with a certain heartbeat, the execution can continue over the succeeding one or more heartbeats to acquire necessary echo signals.

Unless the count in the numbering counter CNT has yet reached its limit, steps S5 to S11 will be processed again. Thus, in the embodiment as in FIG. 4, when the peak of the third R-wave is accomplished, and the delay time $T_{DL}=T_0+T_{inc}=400$ msec passes, the second scan $IMG_{prep2}$ is launched and continued for the given period, echo signals being acquired as well. When the next R-wave appears after the second sequence, and the delay time $T_{DL}=T_0+2\times T_{inc}=500$ msec passes, the third scan $IMG_{prep3}$ starts and continues for the given period, echo signals being also acquired. Likewise, when the next R-wave appears after the third sequence, and the delay time $T_{DL}=T_0+3\times T_{inc}=600$ msec passes, the fourth scan $IMG_{prep3}$ starts and continues for the given period to acquire echo signals as well. Such scan is repeated by desired times, for example, a total of five times to acquire five frames of echo data from the same cross section.

The echo data are sent to the operation unit 10 via the receiver 8R and then the sequencer 5 in turn. The operation unit 10 reconstructs image data in the k-space into image data in the real space by means of a two-dimensional Fourier transform. The reconstructed image data are stored in the storage unit 11 as MRA image data. The host computer 6 responds to, for example, operational signals from the input device 13 so that MRA images are displayed in a dynamic (CINE) mode.

FIGS. 5(a) to (e) represent a plurality of MRA images of which delay signals for the ECG-gating (synchronous timings) were altered and their echo data were acquired and subject to reconstruction. These drawn images which represent the lungs are visualized by hand-tracing actual picture images acquired, provided that a 2D-FASE method (effective TE ($TE_{eff}$)=40 msec, echo train spacing ETS=5 msec, the number of shots=1, slice thickness (ST)=40 mm, the number of slices (NS)=1, the number of addition (NAQ)=1, matrix size=256×256, FOV=40×40 cm, and actual scan time=approx. 500 msec) is used and the phase encoding direction agrees with the longitudinal direction of the drawings (patient's body-axis direction). A flow of blood regarded as an objective entity in the images is the aorta descendens. The delay times $T_{DL}$ are 300 msec in (a), 400 msec in (b), 500 msec in (c), 600 msec in (d), and 700 msec in (e), respectively.

By visual observation of the dynamic-displayed images, the MRA image of (e) is selected because the strength of echo signals emanated from the aorta flow is the highest and the entire aorta are most clearly shown. Compared with the FIG. 5(e) image, the remaining MRA images in FIGS. 5(a) to (d) show the aorta images whose ranges are limited to shorter portions. It is considered that the scanning for those images was done in the states close to flow void phenomena, due to faster speeds of the blood caused by the heartbeats, considerably reducing the echo signal strength. In consequence, concerning the acquisition of MRA images of the aorta flow in the lungs, this experiment shows that the state of FIG. 5(e), i.e., the delay time $T_{DL}=700$ msec is most proper. Thus, it is proved that an optimum ECG-gating synchronous timing is 700 msec delayed from an R-wave peak.

Therefore the operator can visually decide an optimum image, that is, an optimum delay time $T_{DL}$ from a plurality of MRA images obtained with the delay time $T_{DL}$ dynamically altered, and to reflect a parameter for the decided delay time into an imaging scan that will follow.

By the way, in the foregoing ECG-prep scan, the phase-encoding direction is deliberately set to coincide with the running direction of the aorta (i.e., body-axis direction). This setting accomplishes clear images by which information about the running direction (directional performance) of the aorta flow is not reduced or omitted, providing a superior depiction performance, compared to cases where the phase-encoding direction is set to directions other than the aorta running direction. The reason for this is as follows.

Figure 6:
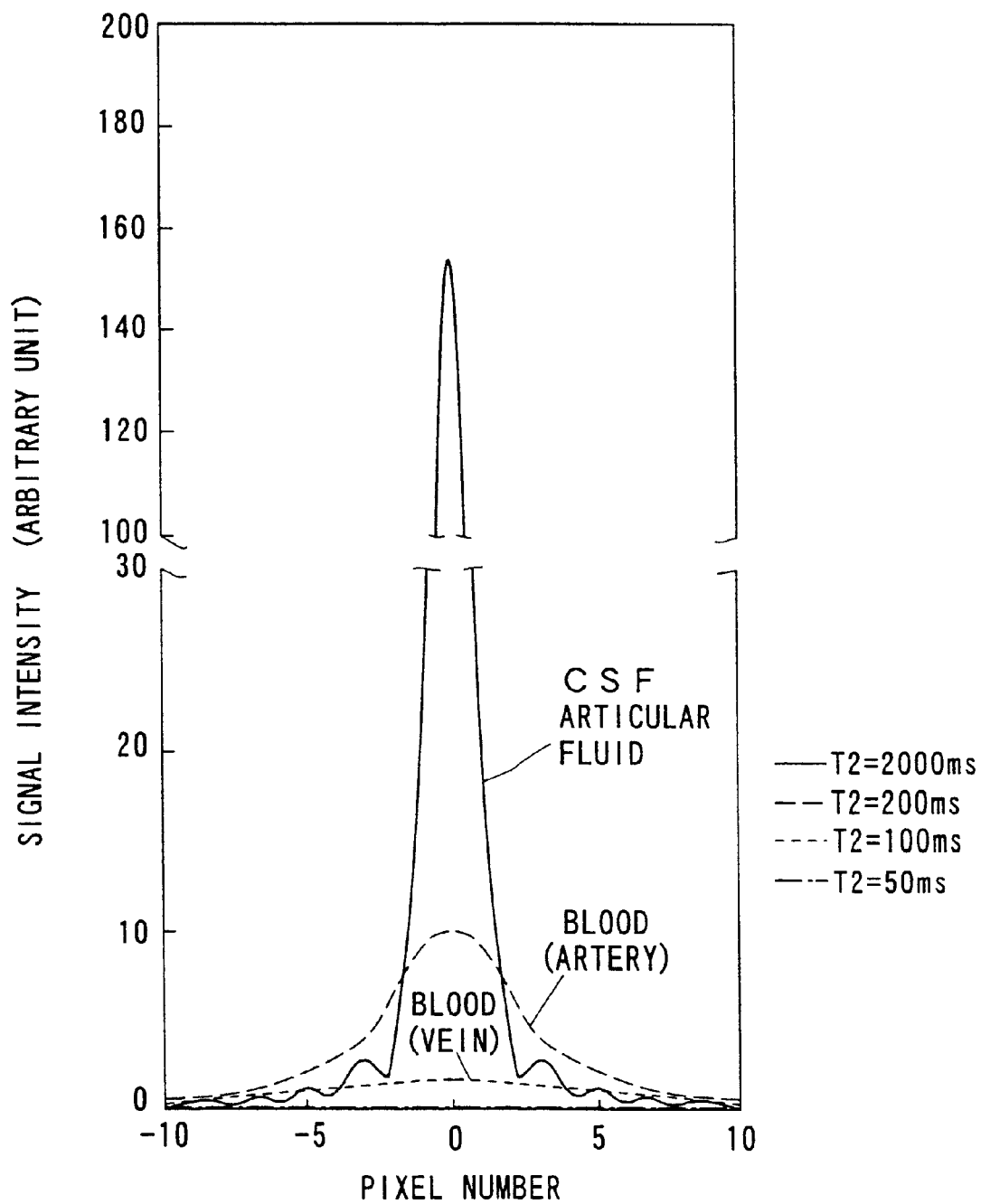
FIG. 6 explains the spread of signals in the phase encoding direction.

In general, a blood flow typical of the pulmonary vessels and hepatic vessels (portal vein) is known to exhibit a rather short time $T_2$ (ranging from 100 to 200 msec). It has been revealed that the half-width of a function of a signal induced by a blood flow exhibiting the rather short time $T_2$ is larger than that of a function of a signal induced by the cerebrospinal fluid (CSF) or articular fluid ($T_2>2000$ msec). This is described in, for example, the literature entitled "The loss of small objects in Variable TE imaging: Implications for FSE, RARE, and EPI" written by R. Todd Constable and John C. Gore (Magnetic Resonance in Medicine 28, 9–24, 1992). According to this literature, the spread of signal levels induced by materials exhibiting different $T_2$ times is, as shown in FIG. 6, expressed by "point spread functions." The graph of FIG. 6 plots the functions observed under the conditions that the static magnetic field strength is 1.5T, $TE_{eff}$ is 240 msec, and the echo train spacing (ETS) is 12 msec. The axis of abscissae indicates the number of pixels in a phase-encoding direction of an image, and the axis of ordinates indicates the signal intensity expressed in any unit. Compared with the function of the signal intensity induced by the CSF or articular fluid exhibiting a $T_2$ time of 2000 msec, the function of the signal intensity induced by blood (artery) exhibiting a time $T_2$ of 200 msec has a larger half-width. It can be said that this is equivalent to situations where the width in phase-encoding direction of the image of the blood (artery) exhibiting the $T_2$ time of 200 msec is apparently stretched than that of the image of the CSF or articular fluid. This means that the whole image of the blood (artery) exhibiting the $T_2$ time of 200 msec is blurred in the phase-encoding direction to a greater extent than that of the CSF or articular fluid.

Thus, by making the phase-encoding direction agree with approximately a blood flow direction, a state in which blood vessels of shorter $T_2$ relaxation times are large than those of longer $T_2$ relaxation times in the degree of spread (blur) of pixels of signal values in the phase-encoding direction can be utilized positively, resulting in enhanced blood flow directions. This facilitates the selection of an optimum MRA image (namely an optimum delay time) for the ECG gating.

Referring to FIGS. 7 to 10, an imaging scan of this embodiment will be described in terms of its operation.

The host computer 6 executes the processes shown in FIG. 7 in response to operational information from the input device 13, as part of the execution of the not-shown given main program.

Specifically, first, the host computer 6 reads from, for example, the input device 13 the optimum delay time $T_{DL}$ determined by the operator through the foregoing ECG-prep scan (step S20). Then, the host computer 6 inputs not only scan conditions (for example, a phase-encoding direction, an image size, the number of scans, a waiting time between scans, and a pulse sequence dependent on a region to be scanned, and others) but also information about an image processing technique (addition or MIP processing, or others: in the case of addition, simple addition, averaging, weighted addition, or others), which have been specified by the operator using the input device 13, processes those bits of information including the delay time $T_{DL}$ into control data, and outputs the control data to both the sequencer 5 and operation unit 10 (step S21).

If it is judged that an instruction indicating the completion of scan preparations has been issued (step S22), a command indicating the start of breath hold is output to the voice generator 16 at step S23. This causes the voice generator 16 to utter a voice message saying "Hold your breath, please." as in the ECG-prep scan. In response to this message, the patient is to hold breathing (refer to FIG. 9).

After this, the host computer 6 instructs the sequencer 5 to start the imaging scan (step S24).

When having received instructions to start the imaging scan (step S24-1), the sequencer 5 begins reading the ECG signal (step S24-2), and determines whether the R-wave (reference wave) peak of the ECG signal has appeared specified n-times on the basis of the ECG trigger signal made synchronous with the peak (step S24-3). The reason why the appearance of the R-wave is waited n-times (for example two times) is that the patient's breath hold can surely be done. When the specified n-time R-wave has appeared, processing to wait for the determined delay time $T_{DL}$ is performed (step S24-4). The delay time $T_{DL}$ is, as explained before, optimized such that echo signal intensities become higher and their depiction performance of an entity become superior, when imaging objective blood flow and tissue on the ECG-prep scan.

Figure 9:
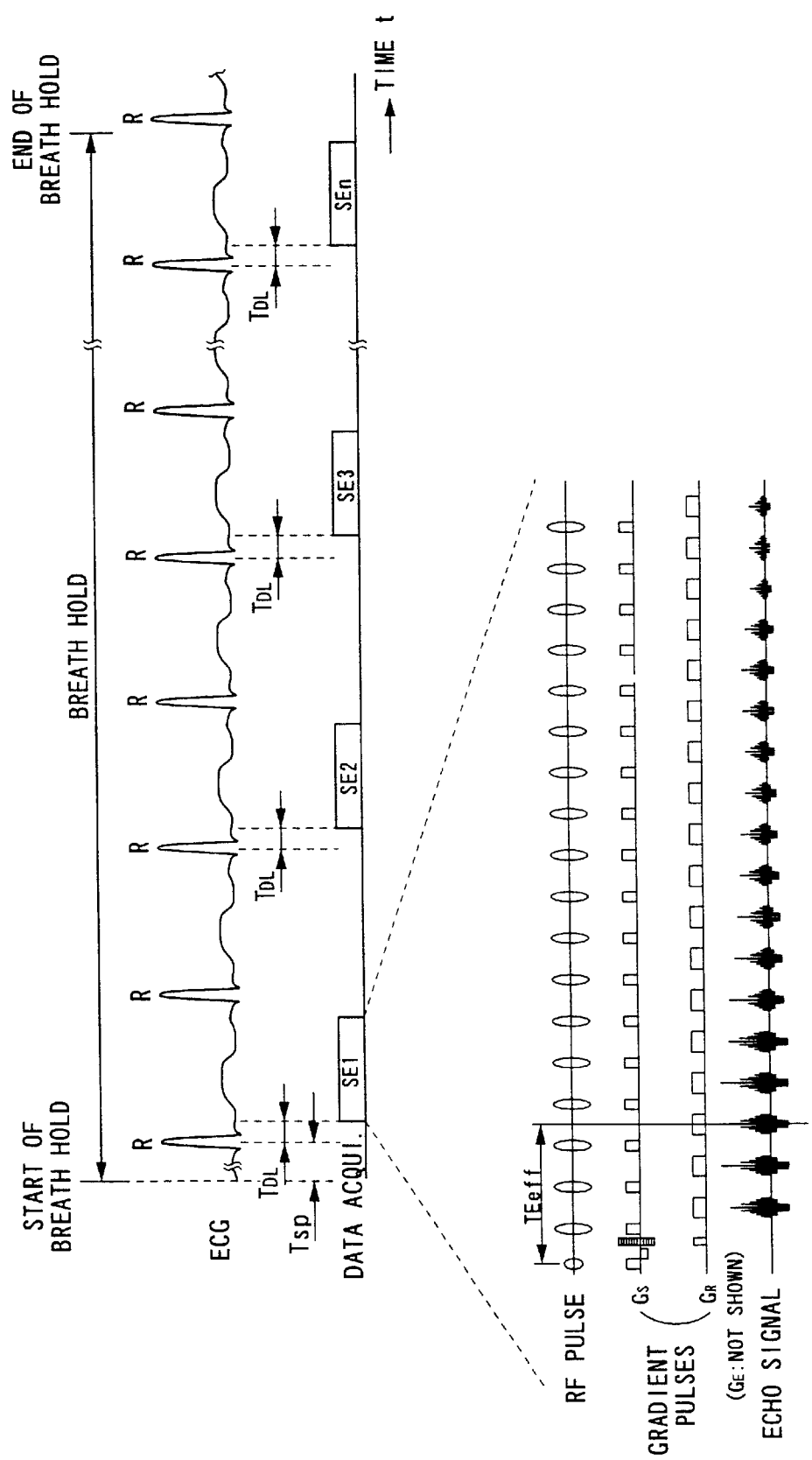
FIG. 9 is a roughly drawn timing chart showing timing of the imaging scan based on the electrocardiogram gating technique in a first embodiment.
Figure 10:
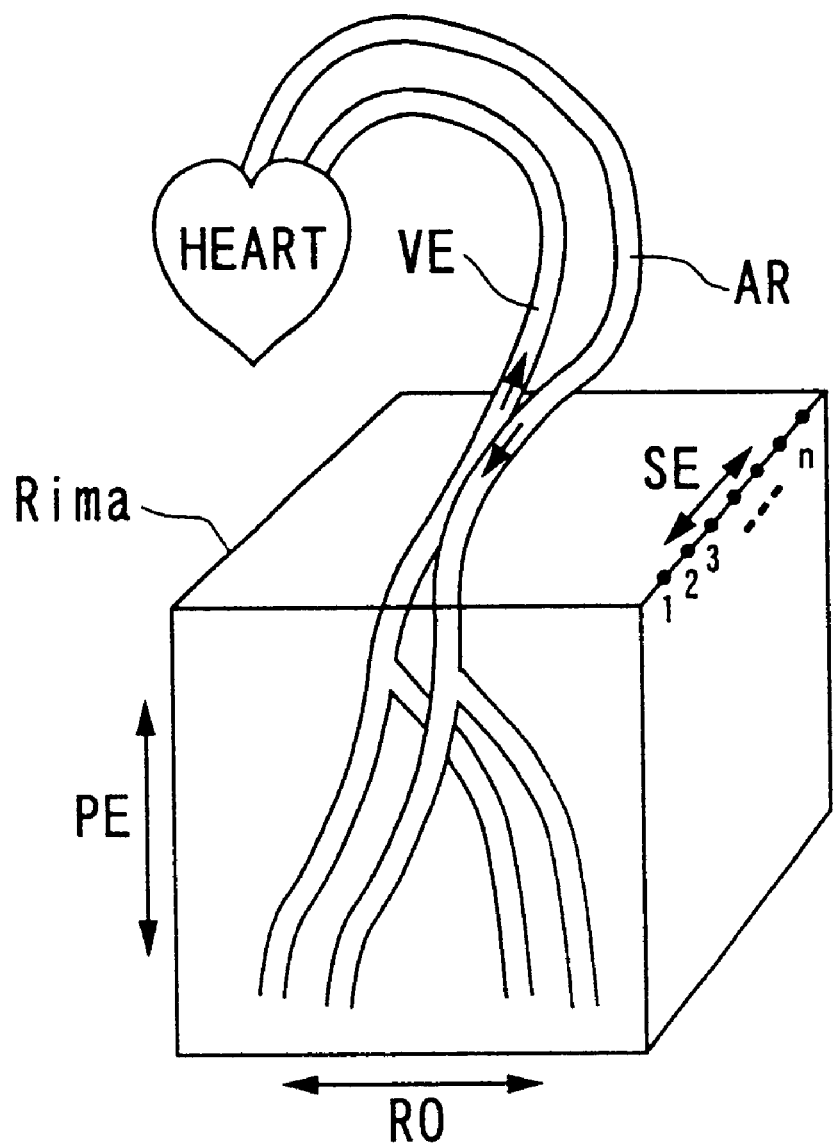
FIG. 10 explains the positional relationship between a three-dimensional imaging volume and each encoding direction.

Regarding as an optimum ECG synchronous timing a time instant when this optimum delay time $T_{DL}$ has passed, the sequencer 5 performs the imaging scan (step S24-5). Practically, the transmitter 8T and the gradient power supply 4 are driven on the pulse sequence information memorized beforehand, so that a scan assigned to the first time is performed with the ECG gating as shown in FIG. 9 according to, for example, a three-dimensional FASE method pulse sequence. (In the figure, the phase-encoding directional gradient is omitted from drawing.) At this time, the phase-encoding direction PE is made to nearly agree with a specified direction, that is, the flowing direction of blood (arteries AR and veins VE), as shown in FIG. 10, for example. Additionally the echo train spacing in the pulse sequence is shortened to 5 msec or thereabouts. Thus, under the first slice encoding amount SE1, echo signals are acquired during a scan time of about 600 msec from a three-dimensional imaging region $R_{ima}$ set to the abdomen as shown in the FIG. 10.

On having completed the first imaging scan, the sequencer 5 determines if the final imaging scan has been completed or not (step S24-6). In the case of NO at this determination (the final scan has not been completed yet), with monitoring the ECG signal, waiting is done until a shortly set period (for example, 2 heartbeats (2R-R) from the R-wave used in the imaging scan) passes, with the result that the recovery of longitudinal magnetization of spins in the stationary parenchyma is actively suppressed (step S24-7). Namely the waiting period forms a repetition time TR.

The repetition time TR is set to a shorter value, compared to a repetition time (approx. 5000 to 8000 msec) adopted in the FASE method for imaging of MRCP and others. This enables the longitudinal magnetization of spins residing in the stationary parenchyma to be relaxed insufficiently on purpose. Differently from the conventional technique, the repetition time TR is set to four heartbeats (4R-R) or less.

In this way, after waiting a period corresponding to, for example, 2R-R, when the third R-wave appears (YES at step S24-7), the sequencer 5 returns its processing to the foregoing step S24-4. Hence, at a time instant when the specified delay time $T_{DL}$ has passed since the generation of the ECG signal synchronous with the third R-wave peak, the second imaging scan is commenced in the same way as the above under the next slice-encoding amount SE2, thus echo signals are acquired from the three-dimensional imaging region $R_{ima}$ (steps S24-4, 5). Likewise, echo signals are acquired until the final slice-encoding amount SEn (for example n=8).

On having completed the final imaging scan under the slice-encoding amount SEn, the determination at step S24-6 becomes YES, thus a notification stating the completion of the imaging scan is sent from the sequencer 5 to the host computer 6 (step S24-6). Accordingly the processing is returned to the host computer 6.

When receiving the notification stating the completion of the imaging scan from the sequencer 5 (step S25), the host computer outputs a command to release the breath hold to the voice generator 16 (step S26). The voice generator 16 then utters a voice message saying, for example, "You can breathe." toward the patient to end the period of breath hold (See FIG. 9).

Therefore, as pictorially shown in FIG. 9, the imaging scan on the ECG gating is performed n-times (e.g., n=8) every 2R-R on the basis of the 3D-FASE method, for example.

Echo signals emanated from the patient P are received by the RF coil 7, then sent to the receiver 8R, ever each time of scan. The receiver 8R processes the echo signals with various kinds of preprocessing, then converts them into digital quantities. The digital echo data are sent via to the sequencer 5 to the calculation unit 10, where they are mapped in a three-dimensional k-space formed by memories. Because the half-Fourier transform method is adopted, data that have not been acquired are obtained by means of calculation, and the calculated data are mapped in the k-space. When the entire k-space is loaded with echo data, a three-dimensional transform is performed, transforming the echo data into real-space image data. The image data are then subject to the MIP processing, producing two-dimensional tomographic image data. The tomographic image data are stored in the storage unit 11 and displayed by the display unit 12.

To confirm advantages of the construction described above, the inventor obtained an actual coronal image of the abdomen to depict the aorta under the following conditions. The static field was 0.5T, a pulse sequence used was a 3D-FASE method based sequence ($TE_{eff}$=24.8 msec, ETS= 6.2 msec), a matrix of 256×256 was subject to 8 slice-encoding amounts, every 3 heartbeats (3R-R), and a coronal image of the abdomen was obtained by the MIP processing. The phase-encoding direction was set to superior-inferior direction (patient's body-axis direction). The ECG delay time was 600 msec. The entire scan time was approx. 23 sec, with one time of breath hold conducted. As a result of this, a superior depiction performance for vessels was confirmed.

In this way, the repetition time TR for each slice encoding is set to shorter values, such as 2R-R or 3R-R. Hence, the longitudinal magnetization in a stationary parenchyma is insufficiently relaxed on purpose, signal values resulting from the parenchyma being suppressed.

Additionally, the ECG gating makes it possible to depict relatively high inflowing speed of blood every heartbeat. Since the ECG gating technique is based on an optimum delay time $T_{DL}$ permitting the scan to be performed every slice encoding during the diastole in which blood flow is stable, the blood flow can be caught in a steady fashion and fresh blood which has just pumped out from the heart can always be scanned. The inventor called this MR angiography an "FBI (Fresh Blood Imaging) technique."

With avoiding a turbulent temporal time that will occur immediately after the R-wave appearance, the scan can be performed during a selected time period in which blood flow states are relatively stable. This makes it possible to eliminate the influences caused by turbulent blood flows and map echo signals acquired in the stable blood flow states in the central part in the phase-encoding direction of the k-space, raising contrast of reconstructed images.

Accordingly, MR angiography with superior depiction performance for blood flows can be provided.

Furthermore, since both the repetition time TR and the echo train spacing are set to shorter values, the phase-encoding direction is almost the same as the vessel running direction, and the slice direction is set along the patient's coronal direction (a direction passing a patient from the front to the back), the entire scan time becomes short, compared to a technique of imaging along a perpendicular direction to blood flows, as seen in TOF method. Also, a range (length) to be imaged in the slice direction becomes short, the number of application times of the slice encode is less, whereby noticeably shortening the entire imaging time, in comparison with the conventional TOF method or phase-encoding method. This provides fewer burdens on patients and increases a patient throughput.

In association with this, because the entire imaging (consisting of a plurality of imaging scans) can be completed within an interval that can be accomplished by one time of breath hold, burdens on patients remarkably diminish.

Since it is not necessary to administer the contrast medium, non-invasive imaging is attained. From this respect, mental and physical burdens on patients are also greatly decreased. Further, an operator is released from troublesome matters inherent to the contrast method, such as measuring timing of contrast effects. Unlike the contrast method, it is possible to repeat imaging, as needed.

Further, because the phase-encoding direction is made to agree or nearly agree with the running direction of vessels, the blurring of pixels can utilized positively, providing an outstanding performance to depict the running direction of vessels. Altering the phase-encoding direction according to the vessel direction running in a portion to be imaged enables to easily image various portions.

Because the pulse sequence originating from the fast SE system is used, there are gains in susceptibility and contour distortion.

Further, the ECG-gating synchronous timing is optimized in advance, almost eliminating the need for re-performance of imaging. Thus, operative burdens on an operator are relieved, it is possible to raise a patient throughput, and burdens on patients are also relieved or lowered.

In the foregoing embodiment, all the imaging scans are completed within an interval of one time of breath hold. Thus, motion artifacts due to cyclic motions of the lungs etc. suppressed. Concurrently, motion artifacts due to positional shifts of patient's body itself generated when the breath hold is performed over a plurality of times are decreased. These contribute to providing high-quality images of fewer artifacts.

According to the foregoing embodiment, a new synthesized image can be obtained from a plurality of images resultant from echo data acquired with the phase-encoding direction altered. This synthesized image can provide a higher performance to depict blood flows, particularly, of which T2 time is shorter, thanks to controlling the phase-encoding direction.

(Second Embodiment)

Figure 11:
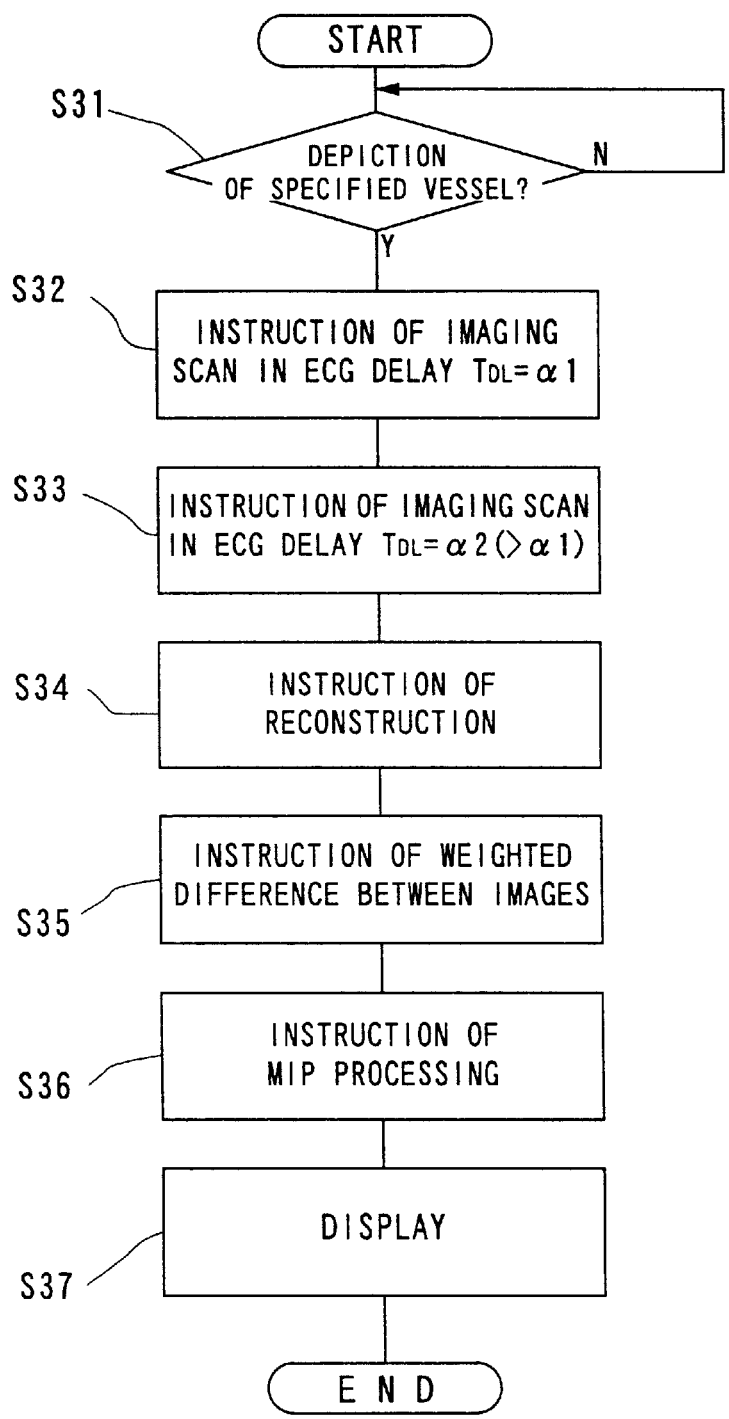
FIG. 11 is an outlined flowchart showing the general processing of the imaging scan in a second embodiment.
Figure 12:
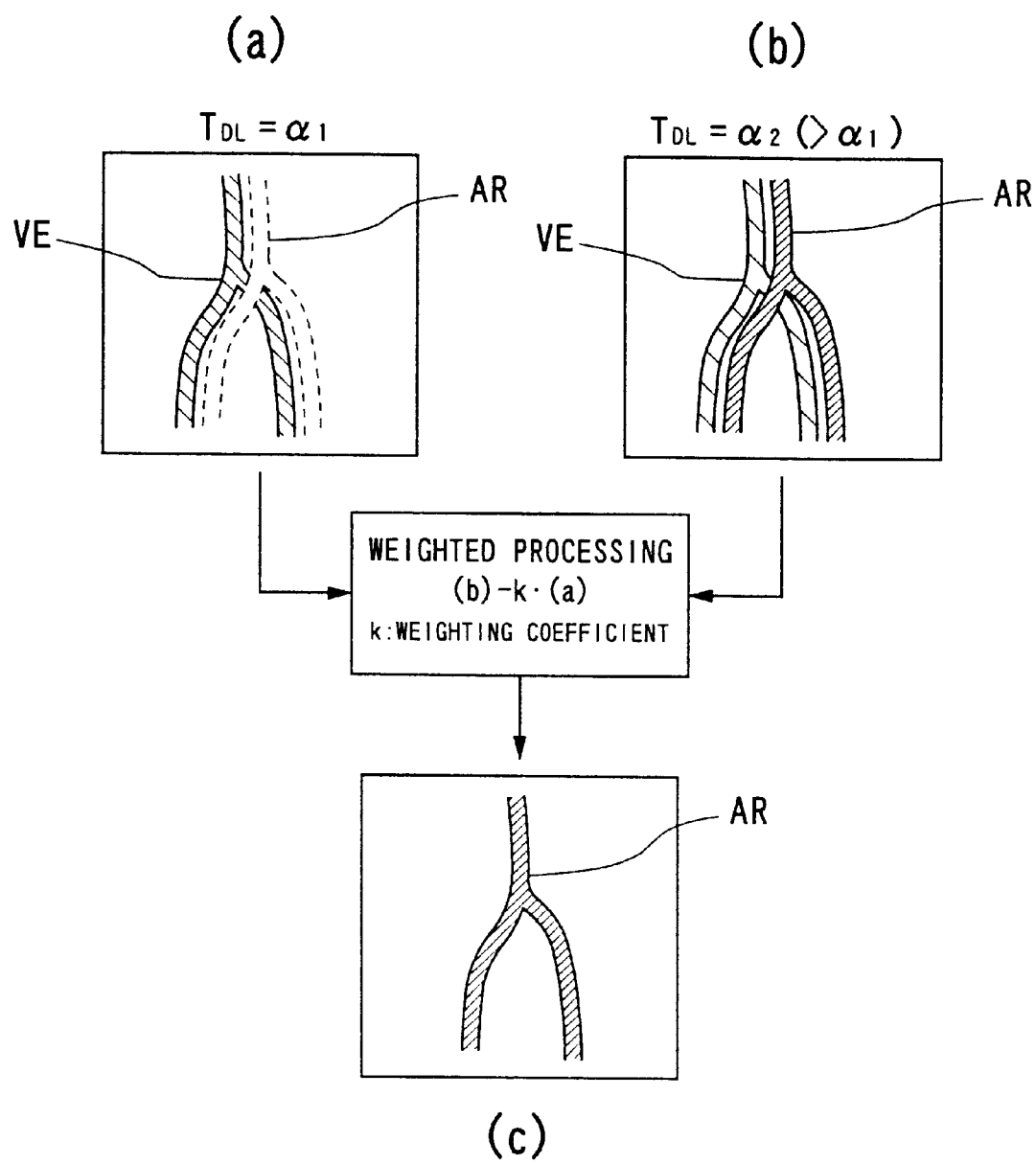
FIG. 12 explains difference calculation for weighting conducted in the second embodiment.

Referring to FIGS. 11 and 12, a second embodiment of the present invention will now be explained. An MRI system of this embodiment is made to be developed more from the configuration of the first embodiment. That is, its feature is that only a specific vessel is depicted by performing not only imaging with the ECG-gating delay time and but also mutual difference with a plurality of MRA original images obtained from the imaging.

The hardware configuration of this embodiment is identical or similar to that explained in the first embodiment.

As outlined in FIG. 11, when instructions to depict a specific vessel, such as the aorta, for example, are generated (step S31), the host computer 6 instructs the sequencer 5 to perform imaging scans under the ECG-gating delay times $T_{DL}=\alpha 1$ (e.g., 100 msec) and $T_{DL}=\alpha 2$ (not equal to $\alpha 1$; e.g., 500 msec) (steps S32, S33). These plural types of delay time $T_{DL}$ can be set adequately, as long as their values differ from each other. According to the type of vessels to be depicted, such delay times can be determined through the ECG-prep scan and memorized beforehand, or an operator can input them as part of imaging conditions every occasion of imaging.

The original data acquired a plurality of times on the basis of each of the plural types of delay time $T_{DL}$ are stored in the calculation unit 10, where the image reconstructing calculation is performed, like the previous embodiment (step S34). The host computer 6 then instructs the calculation unit 10 to execute weighted difference calculation between a plurality of sets of reconstructed image data pixel by pixel (step S35).

An example is pictorially shown in FIG. 12. For example, both a set of three-dimensional image data under the ECG-gating delay time $T_{DL}$=100 msec and another set of three-dimensional image data under the ECG-gating delay time $T_{DL}$=500 msec undergo an weighted difference calculation. As shown in FIG. 12(a), when the ECG-gating delay time $T_{DL}$=100 msec, that is, rather short, the blood pumped out (ejected) becomes turbulent, resulting in flow voids. As a result, signal values of the artery AR becomes almost zero (in actual images, visualized in black), only signals of the vein VE are acquired. In contrast, as shown in FIG. 12(b), on occasions when the ECG-gating delay time $T_{DL}$=500 msec, that is, an appropriate time, signals of both the artery AR and the vein VE are acquired in appropriate intensities. Accordingly, performing mutual weighted difference between image data of FIGS. 12(a) and (b) on the pixel basis provides three-dimensional image data that express only the artery AR as shown in FIG. 12(c). In the case of FIG. 12, for image data of (a) and (b), difference calculation using a weighting coefficient k expressed by "(b)–k·(a)" is done. The weighting coefficient k is determined such that image data of the vein VE are mutually cancelled well by the difference. Then, the host computer 6 instructs the calculation unit 10 to perform the MIP processing with difference-underwent image data (step S36), and have them displayed (step S37). This provides an MRA image where the artery AR is preferably depicted.

Hence it is possible to obtain the similar operation and advantages to those in the first embodiment. In addition, only a desired vessel can be expressed in a steady manner, providing MRA images in which the arteries and veins are visually separated, thus increasing a diagnostic performance.

The difference calculation in the present embodiment may be done such that two sets of three-dimensional original data (k-space data) of which ECG delay times differ from each other undergo the difference, before those difference-undergone data are reconstructed and MIP-processed.

(Third Embodiment)

Figure 13:
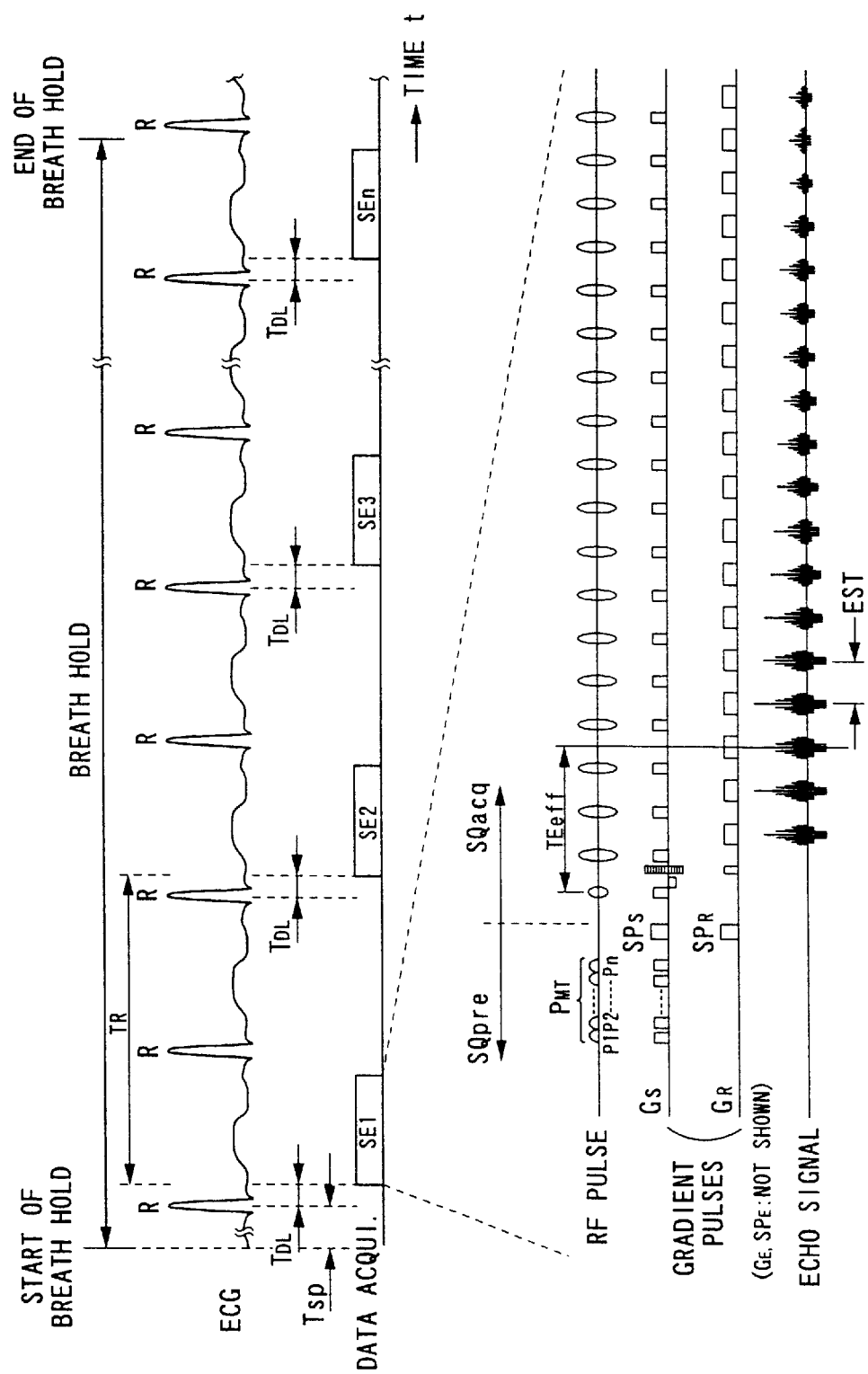
FIG. 13 is a roughly drawn timing chart showing timing of the imaging scan based on the electrocardiogram gating technique in a third embodiment of the present invention.

Referring to FIG. 13, a third embodiment of the present invention will now be explained.

An MRI system according to this embodiment is concerned with another example of the imaging scan on the ECG-gating technique, in particular, with the feature that an MT pulse is applied. As for the FBI technique according to the present invention, the foregoing setting and construction inherent to the FBI technique are inherited.

The hardware configuration and imaging processing are equivalent or similar to those in the first and second embodiments.

In this embodiment, the ECG-gating delay time $T_{DL}$ (synchronous timing) is first set to an optimum using images acquired by the ECG-prep scan, then an imaging scan shown in FIG. 13 is commanded by the sequencer 5 in the similar procedures to the foregoing one. A breath hold technique is also used with this imaging scan.

The rows of pulse sequences shown in FIG. 13 are synchronized with each wave of an ECG signal with a specified delay time $T_{DL}$. The pulse sequence for each shot (RF excitation) is composed of a pre-sequence $SQ_{pre}$ previously executed and a data acquisition sequence $SQ_{acq}$ that follows the previous one.

The pre-sequence $SQ_{pre}$ includes an MT pulse train $P_{MT}$ causing MT effects and gradient spoiler pulses $SP_S$, $SP_R$, and $SP_E$ applied after the MT pulse train $P_{MT}$. The MT pulse train $P_{MT}$ consists of a plurality of exciting RF pulses $P_1$, $P_2$, $P_3$, ..., $P_n$ applied in turn as MT pulses and slice gradients $G_S$ applied in parallel with those MT pulses.

The intensity (=$G_{S1}$) of the applied slice gradients $G_S$ is set in a manner that the MT pulses can be applied to RF-excite an imaging region to be objected in off-resonance. By way of example, a sliced region on the slice gradient $G_S$ is located differently from an imaging region (i.e., $G_S=G_{S2} \neq G_{S1}$) with a gap or gapless.

Each MT pulse $P_1$ ($P_2$, $P_3$, ..., $P_n$) is formed by a SINC function, for example, and its pulse intensity is set so that its spin flip angle FA becomes, for example, 90 degrees. The total number of MT pulses $P_1$, $P_2$, $P_3$, ..., $P_n$ is ten, for example.

In this embodiment, instead of the conventional one MT pulse having a one large flip angle FA (for example, 500 to 1000 degrees) applied slice-selectively, used are a plurality of divided pulses applied consecutively as a train of MT pulses.

An flip angle FA given each MT pulse $P_1$($P_2$, $P_3$, ..., $P_n$) is a divided value (preferably, 90 to 100 degrees) set so that the entire MT pulse train is able to cause desired MT effects. The total number of MT pulses is assigned to an appropriate number (for example, 5 to 10 pieces) in consideration of MT effects given by the entire MT pulse train and a time required to complete the entire imaging. The duration of each MT pulse divided is as short as approx. 1300 μsec, which is shorter by a divided amount than the conventional slice-selective MT pulse.

An interval Δt between the divided MT pulses in the MT pulse train is set so that MT effects for water/fat of parenchyma residing in a region to which the MT pulses are applied can be optimized. This interval Δt depends on regions to be imaged, and if necessary, Δt=0 can be set.

The gradient spoiler pulses $SP_S$, $SP_R$, and $SP_E$ to be applied in the slice, phase-encoding, and readout directions are used as end spoilers in the pre-sequence $SQ_{pre}$. Each gradient spoiler pulse dephases spins in each direction after a plurality of divided MT pulses have been applied, excluding spin mutual interference between the pre-sequence and the data acquisition sequence, thus preventing occurrence of stimulated echoes. This spoiler pulse can be applied only in any one or two directions.

The data acquisition sequence $SQ_{acq}$ is formed in the same way as that described in the foregoing FIG. 9.

Since a plurality of divided MT pulses $P_1$, $P_2$, $P_3$, ..., $P_n$ are used, echo signals from parenchyma (stationary portion) of an imaging region decrease due to MT effects and MT effects generated in blood flows (arteries and/or veins) inflowing into the imaging region is lessened (decreased). In other words, a plurality of divided MT pulses cause the longitudinal relaxation T1 time of flowing or tumbling blood to be shortened apparently, thereby lowing MT effects in their effectiveness. Meanwhile, the parenchyma (stationary portion) receives signal-lowering effects corresponding to the sum of a plurality of divided MT pulses. Therefore, image contrast between inflowing blood (blood) to the imaging region and its parenchyma remarkably rises, compared to use of MT effects generated by the conventional single MT pulse (its duration is longer and its flip angle is larger).

In consequence, according to the present invention, in addition to the operation and advantages based on the foregoing FBI technique, there are provided MRA images with not only fewer artifacts but also remarkably improved degrees of image contrast between inflowing blood/parenchyma compared to the conventional MT pulse.

Figure 14:
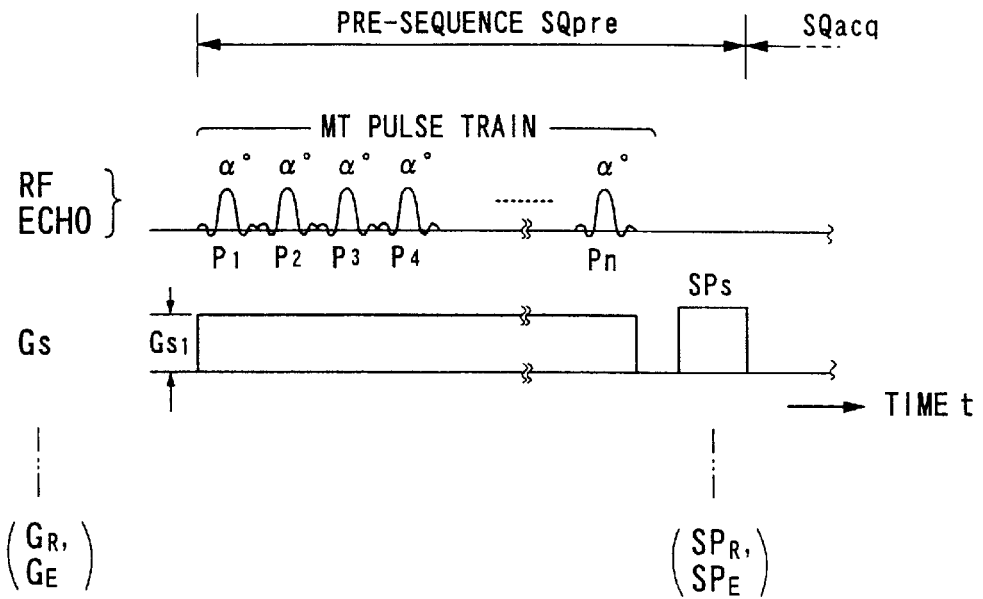
FIG. 14 is a partially drawn timing chart showing another application technique of divided MT pulses.
Figure 15:
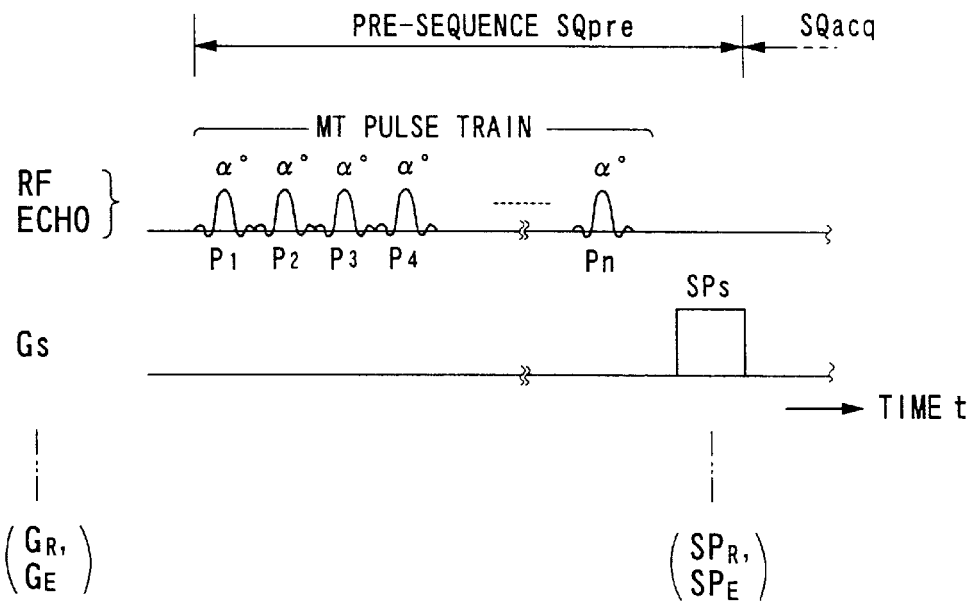
FIG. 15 is a partially drawn timing chart showing still another application technique of divided MT pulses.

The technique for applying a plurality of divided MT pulses is not restricted to that in FIG. 13, but can be practiced into modified examples shown in FIGS. 14 and 15.

According to the application method shown in FIG. 14, instead of a plurality of slice gradient pulses $G_S$ applied concurrently with a plurality of divided MT pulses, only one slice gradient pulse $G_S$ is continuously applied over the entire application period of a plurality of divided MT pulses. This is able to shorten a time necessary for applying the MT pulse train $P_{MT}$, realizing a shorter imaging time. In the case of the application method shown in FIG. 15, no gradient pulse is applied in any direction; the divided MT pulses are applied alone. Thus a plurality of divided MT pulses are applied in a slice-non-selective fashion. So the divided MT pulses are applied to a wider area, not limited to whether a region to be imaged is a slice or slab. In FIGS. 14 and 15, gradient pulses in the readout and phase-encoding directions are omitted from drawing.

(Fourth Embodiment)

Figure 16:
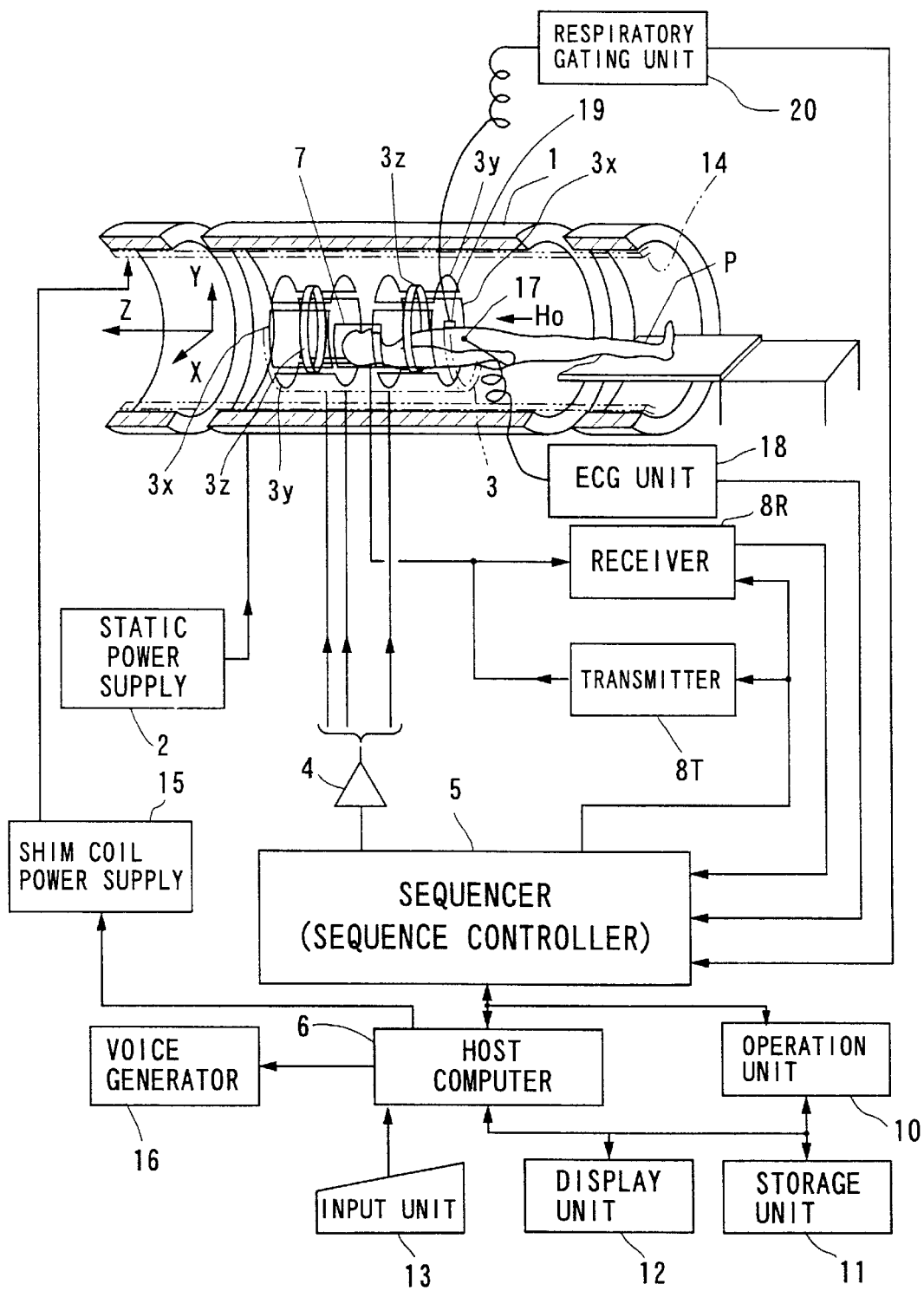
FIG. 16 is a functionally illustrated block diagram showing the configuration of an MRI system according to a fourth embodiment of the present invention.
Figure 17:
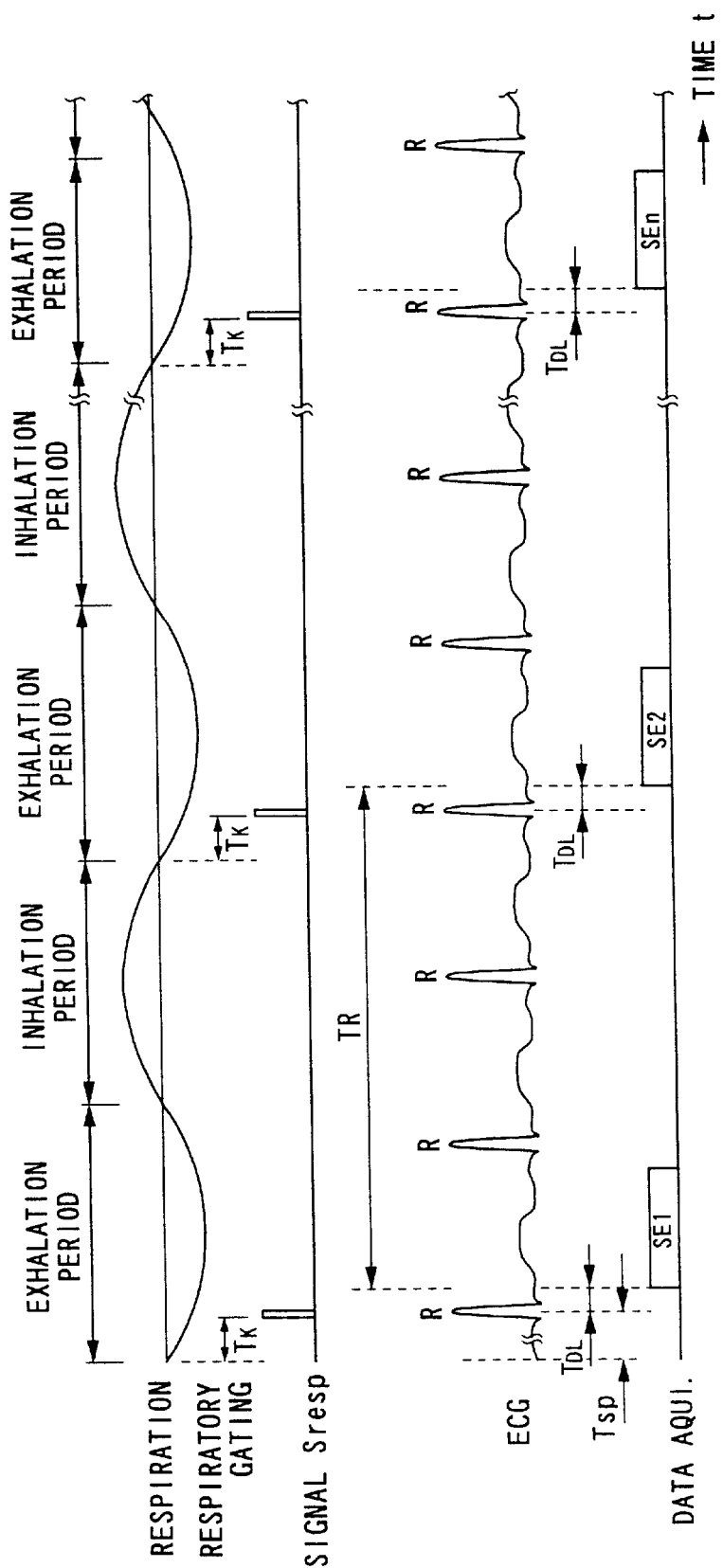
FIG. 17 is an outlined timing chart showing timing of an imaging scan using both electrocardiogram gating and respiratory gating techniques in the fourth embodiment.

Referring to FIGS. 16 and 17, a fourth embodiment of the present invention will now be described.

An MRI system of this embodiment features to use a respiratory gating technique in combination with the forgoing ECG gating technique.

As shown in FIG. 16, the MRI system is additionally provided with a respiratory sensor (electrode) 19 not only being placed on the pectoral region of an object but also detecting a signal proportional to its thorax motion, and a respiratory gating unit 20 not merely calculating respiratory profile data from the signal by detected by the sensor 19 but also outputting a synchronous signal made to synchronize with a desired period (for example, an exhalation period) in respiratory cycles of the object. The respiratory sensor and the respiratory-gating unit may be constructed into other ways; for example, they may be a construction in which the motion of the abdominal muscle is detected as optical amounts to obtain the respiratory cycle, or an apparatus is used in which a flow of gas flow associated with the respiration is detected with rotary vanes.

A respiratory gating signal outputted from the respiratory gating unit 20 is sent to the sequencer 5. Using both the ECG signal and the respiratory gating signal, the sequencer 5 performs the imaging scan described in the foregoing embodiments. The other constructions of the MRI system are identical to those described before.

As shown in FIG. 17, the sequencer 5 monitors the passing of a specified delay time $T_k$ from, for example, the beginning of the exhalation period of the respiratory motion. When the delay time $T_k$ has passed, then monitored is a timing of another delay time $T_{DL}$ which passes from an R-wave of the ECG signal that will appear after the passing of the former delay time $T_k$. In response to the timing gained, the scan is performed every slice encode, as described before.

In consequence, a three-dimensional scan can be performed on the FBI technique using in combination both the ECG and respiratory gating techniques. Hence, in addition to various operative features achieved by the forgoing FBI technique, imaging can be provided in which burdens on an object are lessened, because the object is unnecessary to perform one's breath hold. Operator's operative burdens associated with instructions for breath-hold decrease as well.

(Fifth Embodiment)

Figure 18:
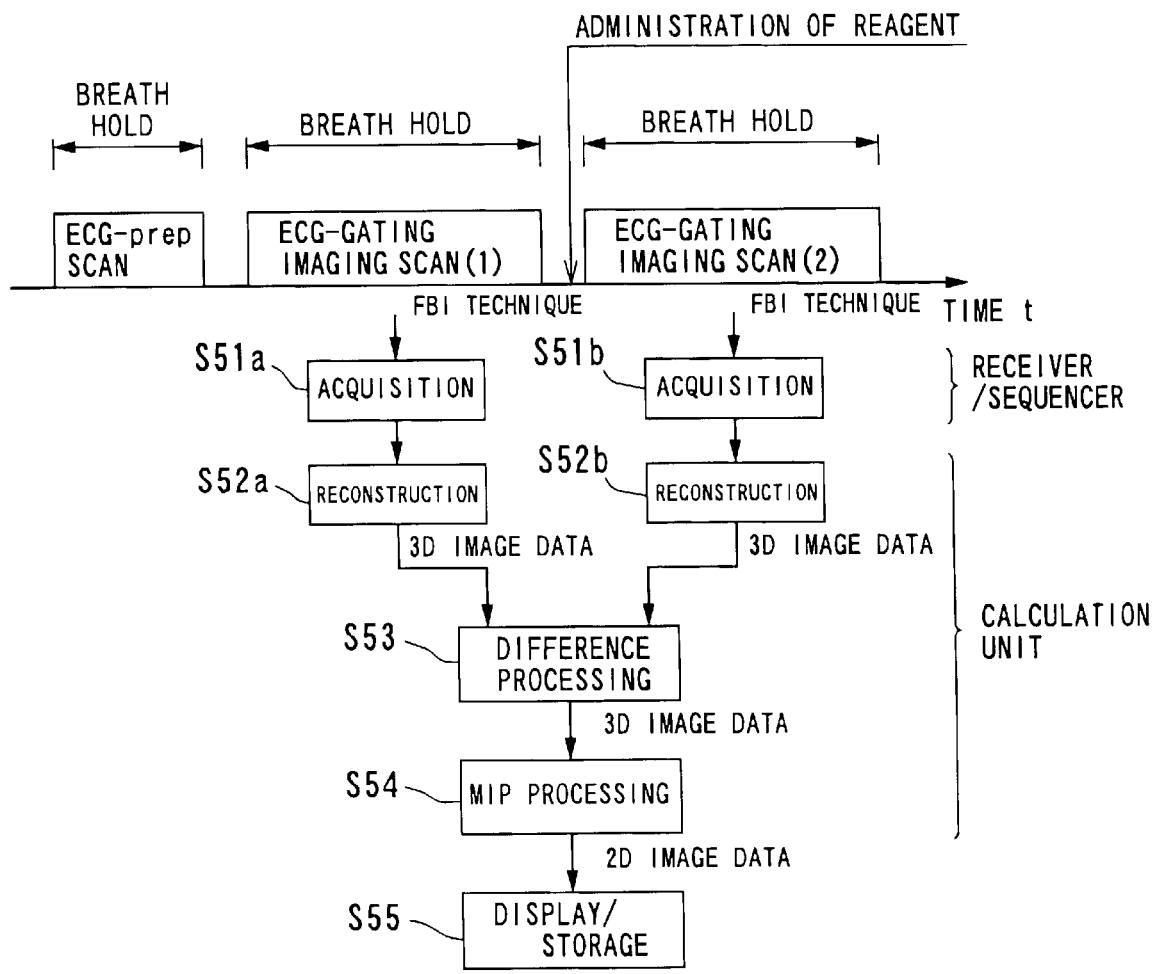
FIG. 18 is an explanation showing an outline of processing of acquired data and imaging procedures in a fifth embodiment of the present invention.
Figure 19:
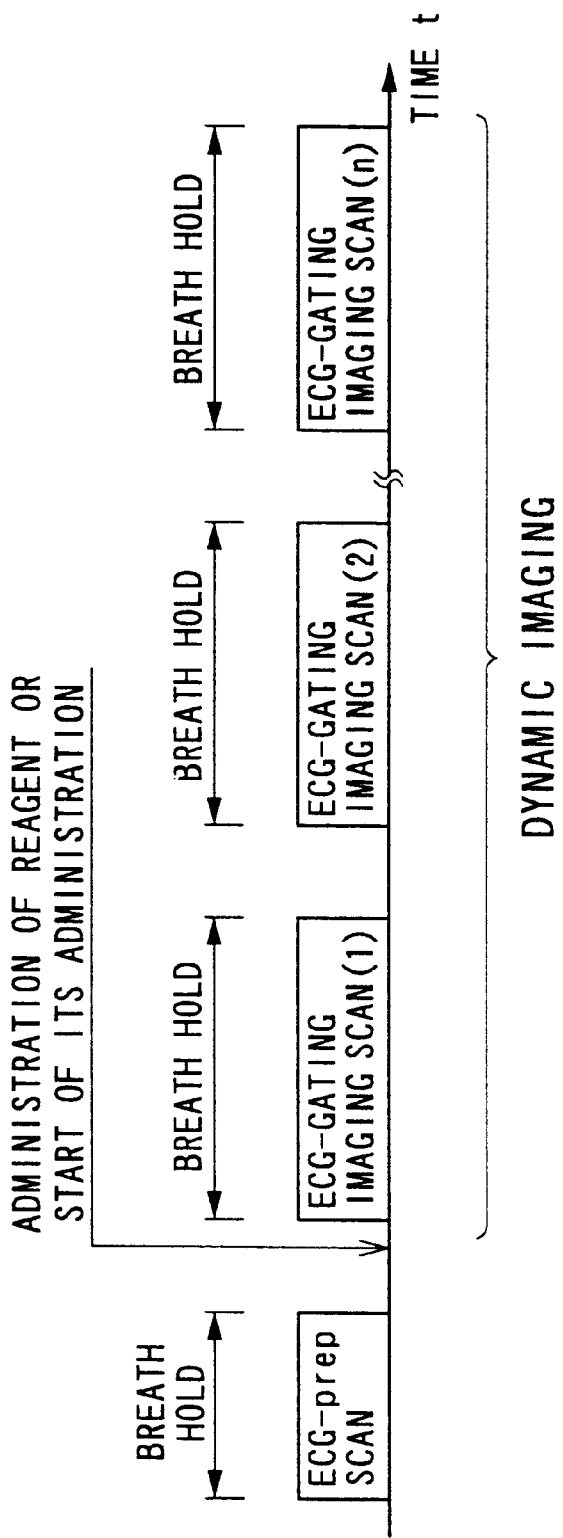
FIG. 19 is an outlined explanation showing imaging procedures in another embodiment.
Figure 20:
FIG. 20 shows a pictorially sketched explanation of an experimental example in the fifth embodiment.
Figure 20:

Referring to FIGS. 18–20, a fifth embodiment of the present invention will now be described.

The present embodiment features a construction in which various reagents can be injected into an object and the contrast effects of the reagents or functions of the object stimulated by the injected reagents-are imaged.

The reagents used in the present invention, which are different from MR contrast mediums which have been used conventionally, include injection agents such as physiological saline or glucose, and potable agents such as or including acetic acid, that is, oral-administration type of regents. In the case of using the former injection agents, their contrast effects contribute to imaging. As to the latter potable agents, it is preferred that other adequate constituents are mixed with the acetic acid to make patient's drinking easy.

FIG. 18 exemplifies a fundamental sequence according to an imaging technique to which the reagent administration is applied, in addition to a flow of image production. The sequence is performed by both the sequencer 5 and the calculation unit 10 under the control of host computer 6. The performance of the scan based on the sequence and the data processing for the image production are identical or similar to those described in the foregoing embodiments.

First, the foregoing ECG-prep scan is performed, and an optimum delay time $T_{DL}$ for the ECG gating is obtained. A before-reagent-administrating ECG-gating imaging scan (1) is then performed on the foregoing FBI technique. In this imaging scan (1), the breath hold is instructed.

A reagent is then administered into an object. If the reagent is physiological saline or glucose, it is administered by 100 cc or thereabouts by injection, as an example. In the case that the regent is a potable agent such as or including acetic acid, it is oral-administered by 10 cc or thereabouts. After this administration, waiting is done for an adequate time. An after-reagent-administrating ECG-gating imaging scan (2) is then performed on the foregoing FBI technique. In this imaging scan (2), the breath hold is instructed.

As both the pulse sequence used in these two-times of imaging scans, preferable is a sequence which can obtain enhancement effects due to blurring of the T2 time described before a three-dimensional scan method based on the FSE, FASE, EPI, or others, for example.

By the way, it may be possible to adopt a construction in which imaging is performed on the TOF or PS method with a reagent administered.

When the physiological saline or glucose is injection-administered as a reagent, the T2 time of blood rises, that is, the T2 relaxation time become longer, producing contrast effects. As a result, echo signal intensities detected from the blood increase, improving an SNR. Meanwhile, in the case that a potable agent such as or including acetic acid is used as a regent, a constituent of acetic acid in the administered potable agent stimulates (reflects) a vessel system, especially, a portal system, expanding the vessel. Consequently, because an amount of blood flow rises, echo signal intensities detected from the blood increase, improving an SNR.

Echo signals generated by each of these imaging scans are acquired into the calculation unit 10 thorough the receiver 8R and sequencer 5, thus being reconstructed into three-dimensional image data (FIG. 18; steps S51a, S51b, S52a, and S52b). The two sets of three-dimensional image data are then subjected to difference processing done between the data sets by the calculation unit 10 pixel by pixel, by way of example (step S53). Then, the resultant data from the difference undergo MIP processing, before their display and storage are done (step S54 and S55).

FIG. 19 shows a sequence flow of a dynamic scan performed after the administration of a reagent. After having administered a reagent or having begun to administer a regent, a volume region is imaged with a three-dimensional scan at intervals, and time-changing data concerning the regent residing in the body are determined. To the three-dimensional scan, applied is a pulse sequence on the FBI technique on a three-dimensional Fourier transform method, or, a multi-slice sequence (of which ECG-gating delay time for each slice is the same) of the FBI technique on a two-dimensional Fourier transform method.

The inventor experimentally confirmed the advantages obtained when this reagent administration is actually applied to the FBI technique. In one experiment, physiological saline was administered by an amount of approx. 150 cc by injection. And before-and-after images of the pulmonary field were imaged using a 1.5T (stationary field) MRI system for comparison. A pulse sequence used in this experiment was a 3D-FASE method sequence of which imaging parameters were; $TE_{eff}$=60 msec, TR=3R-R, TI=180 msec, matrix size=256×256, ETS=5 msec, FOV=37 cm×37 $cm^2$, and resolutions=1.4 mm(RO)×1.4 mm(PE)/2 mm(slice). This experiment showed that differences in signal intensities from the pulmonary arteries were clear and depiction ability for thin vessels was improved. It is considered that these effects are attributed to the fact that a constituent of water is administered into the vessels, which lowers the influence of blurring due to the T2 time. Thus the vessels were sharply depicted.

The other experiment was conducted; acetic acid was oral-administered by an amount of approx. 20 cc. And before-and-after images of the abdominal and pectoral region were imaged using a 0.5T (stationary field) MRI system for comparison. A pulse sequence used in this experiment was a 3D-FASE method sequence of which imaging parameters were; $TE_{eff}$=62 msec, TR=3R-R, TI=140 msec, matrix size=256×256, ETS=6.2 msec, FOV= 37 cm×37 $cm^2$, and resolutions=1.4 mm(RO)×1.4 mm(PE)/2 mm(slice). FIGS. 20(a) and 20(b) show pictorial illustrations both drawn by sketching by hand the actually obtained images by the above experiment. FIG. 20(a) is an illustrated image obtained before administering acetic acid, whilst FIG. 20(b) is an illustrated image obtained after administering acetic acid. As understood from the comparison, compared to the before-administration image, in the after-administration image, it was confirmed that there were remarkable signal differences of the vessels and the depiction ability for the vascular system was largely raised. This is because, as described before, a constituent of acetic acid stimulated the portal system. Additionally, this stimulation permitted vessels in the stomach to be depicted. Thus it wad found that vessels were functionally measured depending on the type of administered stimuli (reagents).

In particular, in the after-administration image of FIG. 20(b), even an extremely thin vessel $B_{thin}$ was visualized, which was not shown in the before-administration image of FIG. 20(a) at all. In cases where MT angiography by which an MR contrast medium Gd-DTPA is administered is performed, thin vessels such as collateral vessels are independent on time-changes of contrast effects. Thus, even if a collateral vessel is built due to a constriction or others formed on a vessel, such collateral vessel cannot be depicted by the contrast angiography. By contrast, it can be expected that the imaging based on the FBI technique with administering acetic acid be capable of depicting such collateral vessels.

Conventionally, there have been known methods, such as the BOLD (Blood Oxygenation Level Dependent), that perform functional MRI on changes in T2* (apparent T2 time). However, these were not imaging techniques that make it possible to directly observe functions of vessels as images. Such direct observation can be done by the present invention.

If using a reagent such as or including acetic acid, functions of vessels can be included into objects to be imaged. As a result, changes of vessel functions of patients who suffer from functional disorders or diseases of vessels, which have been unable to be depicted yet, can also be imaged.

As one of the above reagent administration technique, vasodilators or blood pressure controlling agents can be used in imaging vessel disease portions as the reagent according to the invention. This enable the performance of functional MRA before and after administering the reagent toward patients who suffer from varicosis or others as well as the depiction of a vascular network of patients who have collateral vessels on account of constriction or others.

In the case of CE-MRA method with administering Gd-DTPA, it is reported that a constriction is underestimated (refer to "NICHIJIISHI 17:4; 115–124, 1995). To avoid such underestimation, an imaging on to the FBI technique according to the present invention can be adopted. Namely, with physiological saline administered, an imaging on the FBI technique is simply performed. Hence, the physiological saline acts as a contrast medium, making the T2 time of vessels longer to some extent, reducing blurring of the T2 time. The condition in which the constriction is underestimated is excluded in most cases.

Although the above embodiment is constructed such that the imaging using the reagent is conducted on the FBI technique, the respiratory gating is incorporated in this construction.

Figure 21:
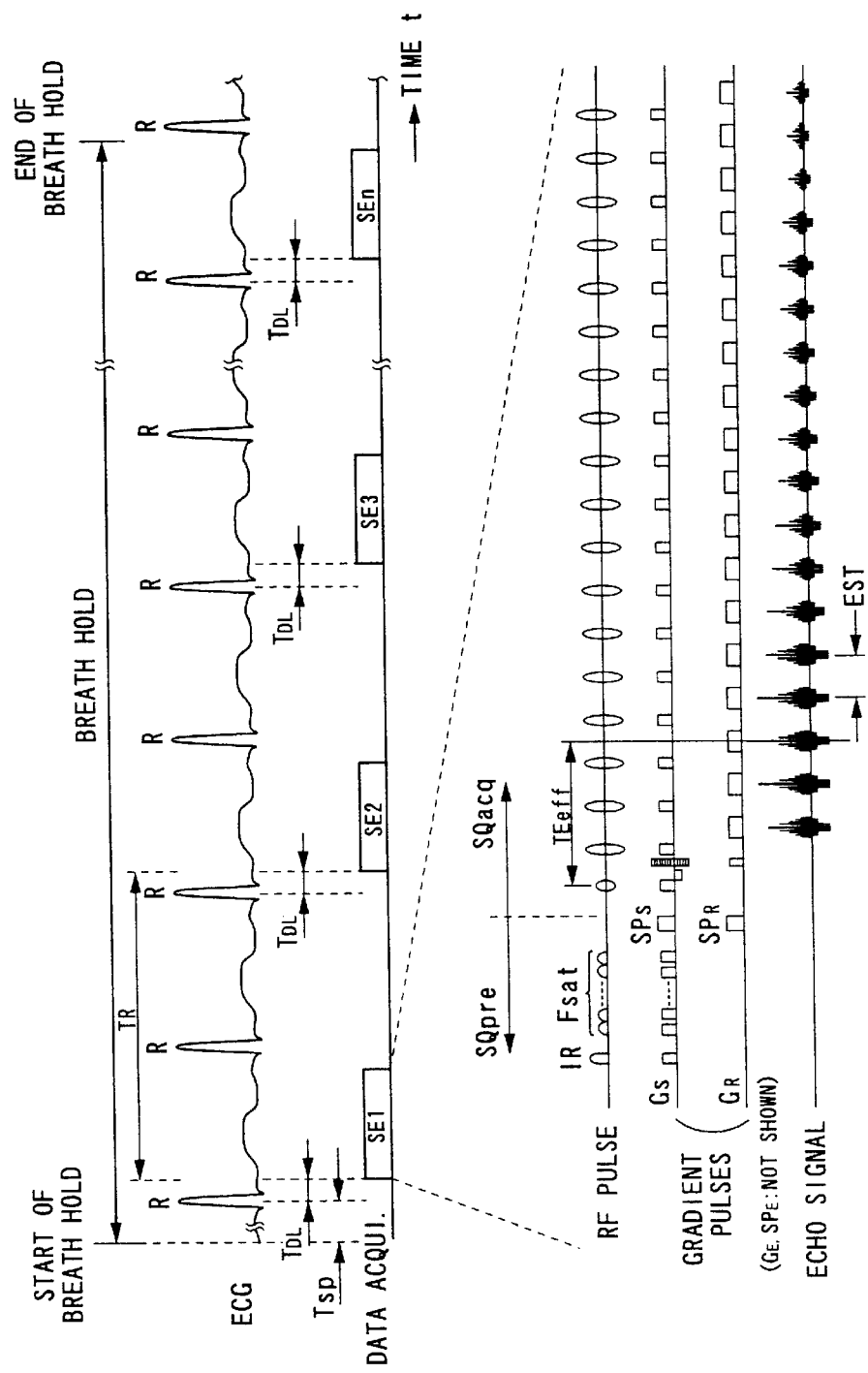
FIG. 21 is a timing chart showing another example of a pulse sequence according to the present invention.

In the present invention, a pulse sequence shown in FIG. 21 can be applied to the foregoing three-dimensional scanning pulse sequence, where, before performing an imaging data acquisition sequence, an inversion recovery IR pulse and/or fat suppression pulses $F_{sat}$ are applied to suppress MR signals of fat in an imaging region from being acquired.

Though the embodiments have been explained as the above, the present invention is not confined to the constructions explained by such embodiments. The person skilled in the art may alter or modify it in adequate fashions within the scope described in the claims, and such altered or modified constructions should be included in the present invention.

As described above, according to MR angiography of the present invention, a signal indicative of cardiac temporal phases of an object is acquired, and a three-dimensional scanning pulse sequence is performed every slice encode toward an imaging region of the object in a synchronous state with reference waves. Accordingly, it is not required to administer a contrast medium. With a non-invasive condition, MRA images of which ability to depict vessel-running directions is high can be provided. Additionally, the pulse sequence includes an RF excitation pulse of which repetition time is set to be shorter, the phase-encoding direction is nearly in agreement with a vessel-running direction, and the slice direction is set to a direction perpendicular to the vessel-running direction, for example, the front-and-back direction of the object. These make it possible to acquire data in a nearly parallel direction to the vessel-running direction every slice encode, reducing an imaging time largely. In addition, there are provided images in which arteries and veins are separately depicted.

Moreover, performing the above technique with a reagent that promotes contrast effects of blood or stimulates vessels leads to improvement in the S/N of blood flow images as well as direct imaging of functions of vessels.

What is claimed is:

1. An MRI system for obtaining a blood flow image of a region to be imaged of an object, said system comprising:
    temporal phase detecting means for detecting a signal indicative of a particular cardiac temporal phase of the object;
    scan performing means for performing a three-dimensional pulse sequence for said region of the object, the three-dimensional pulse sequence being repeated a plurality of times with slice encodes incorporated in the three dimensional pulse sequence being changed in synchronism with each of a plurality of mutually different image delay times set with respect to the signal indicative of a particular cardiac temporal phase;
    echo data acquiring means for acquiring a plurality of sets of three-dimensional echo data generated respectively in response to the repeated performance of the three-dimensional pulse sequence; and
    data processing means for processing the plurality of sets of echo data into date of the blood flow image in which both an artery and a vein of the object are visually separated from each other.

2. The MRI system of claim 1, wherein the plurality of different data delay times is two in number and the plurality of sets of three-dimensional echo data is two in number.

3. The MRI system of claim 2, wherein the data processing means comprises difference calculating means for performing mutual subtraction between two sets of data related to the echo data with the use of a weighted difference so that one set of difference data is produced and producing means for producing the one set of different data into the blood flow image.

4. The MRI system of claim 3, wherein the data processing means comprises image reconstructing means for reconstructing the two sets of echo data into two sets of image data to be provided to the difference calculating means as the two sets of echo-related data.

5. The MRI system of claim 4, wherein each of the two sets of echo-related data includes the three-dimensional echo data.

6. The MRI system of claim 5, wherein the producing means is configured as means for performing a maximum intensity projection on the one set of difference data converted to image data by the image reconstructing means.

7. The MRI system of claim 1, further comprising breath holding instructing means for instructing the object to hold one's breath during a period of time through which the scan performing means performs the pulse sequence.

8. The MRI system of claim 1, further comprising breath cycle detecting means for detecting a breath cycle of the object,
    wherein the scan performing means is configured as means for performing the pulse sequence in synchronism with both of each of the plurality of different imaging delay times set to the signal indicative of the particular cardiac temporal phase of the object and the breath cycle of the object detected by the breath cycle detecting means.

9. The MRI system of claim 1, wherein the three-dimensional pulse sequence includes a slice gradient pulse for data acquisition based on the slice encodes applied in an approximately parallel direction to a running direction of a blood flow in the object.

10. The MRI system of claim 1, wherein the three-dimensional pulse sequence includes a phase-encode gradient pulse for applying a phase encode in a direction approximately coinciding with a running direction of a blood flow in the object.

11. The MRI system of claim 1, wherein:
    the temporal phase detecting means is configured to acquire an ECG signal of the object including the signal indicative of the particular cardiac temporal phase, and
    the scan performing means is configured to perform the three-dimensional pulse sequence in synchronism with an R-wave appearing in the ECG signal, the R-wave corresponding to the signal.

12. The MRI system of claim 11, further comprising:
    preparing scanning means for acquiring a plurality of sets of echo signals by performing a preparing scan within the region of the object at each of mutually different preparing delay times set to the R-wave of the ECG signal;
    preparing-image producing means for producing a plurality of preparing images from the echo signals; and
    providing means for providing the scan performing means with, as the plurality of different imaging delay times, a plurality of optimum delay times selected from the mutually different preparing delay times on the basis of the plurality of preparing images.

13. The MRI system of claim 1, wherein the three-dimensional pulse sequence consists of any one pulse train selected from the group consisting of an FSE based pulse train, FASE based pulse train and EPI based pulse train.

14. An MR imaging method for obtaining a blood flow image of a region to be imaged of an object, said method comprising:
    performing a three-dimensional pulse sequence for said region of the object, the three-dimensional pulse sequence being repeated a plurality of times, with slice encodes incorporated in the pulse sequence being changed in synchronism with each of a plurality of mutually different imaging delay times set with respect to a signal indicative of a particular cardiac temporal phase of the object;
    acquiring, by performing the three-dimensional pulse sequence, a plurality of sets of three-dimensional echo data generated respectively in response to the repeated performance of the three-dimensional pulse sequence; and
    processing the plurality of sets of echo data into data of the blood flow image in which both an artery and a vein of the object are visually separated from each other.

15. The MR imaging method of claim 14, wherein the plurality of different imaging delay times is two in number and the plurality of sets of three-dimensional image data is two in number.

16. The MR imaging method of claim 15, wherein the processing step includes the steps of:
    performing subtraction between two sets of data related to the echo data with the use of a weighted difference so that one set of difference data is produced; and
    producing from the one set of difference data the blood flow image.

17. The MR imaging method of claim 16, wherein the producing step is a step of performing a maximum intensity projection (MIP) with the one set of difference image data.

18. An MRI system for obtaining a blood flow image of a region to be imaged of an object, said system comprising:
- a temporal phase detecting unit configured to detect a signal indicative of a particular cardiac temporal phase of the object;
- a scan performing unit configured to perform a three-dimensional pulse sequence for said region of the object, the three-dimensional pulse sequence being repeated a plurality of times with slice encodes incorporated in the three dimensional pulse sequence being changed in synchronism with each of a plurality of mutually different imaging delay times set to the signal indicative of a particular cardiac temporal phase;
- an echo data acquiring unit configured to acquire a plurality of sets of three-dimensional echo data generated respectively in response to repeated performance of the three-dimensional pulse sequence; and
- a data processing means unit configured to process the plurality of sets of echo data into date of the blood flow image in which both an artery and a vein of the object are visually separated from each other.

19. The MRI system of claim 18, wherein the plurality of different imaging delay times is two in number and the plurality of sets of three-dimensional image data is two in number.

20. The MRI system of claim 19, wherein the data processing unit is configured to (a) reconstruct the two sets of echo data into two sets of image data, (b) perform subtraction between the two sets of image data with the use of a weighted difference so that one set of difference data is produced, and (c) produce from the one set of difference data the blood flow image.

* * * * *